US008420600B2

(12) United States Patent
Burch et al.

(10) Patent No.: US 8,420,600 B2
(45) Date of Patent: Apr. 16, 2013

(54) INJECTABLE CAPSAICIN

(75) Inventors: Ronald Burch, Wilton, CT (US);
Richard B. Carter, Washington Crossing, PA (US); Jeff Lazar, Austin, TX (US)

(73) Assignee: Vallinex, Inc., Baltimore, MD (US)

( * ) Notice: Subject to any disclaimer, the term of this patent is extended or adjusted under 35 U.S.C. 154(b) by 1166 days.

(21) Appl. No.: 11/499,995

(22) Filed: Aug. 7, 2006

(65) Prior Publication Data

US 2007/0036876 A1    Feb. 15, 2007

Related U.S. Application Data

(62) Division of application No. 10/742,621, filed on Dec. 18, 2003, now abandoned.

(60) Provisional application No. 60/434,453, filed on Dec. 18, 2002, provisional application No. 60/434,530, filed on Dec. 18, 2002, provisional application No. 60/434,500, filed on Dec. 18, 2002, provisional application No. 60/434,828, filed on Dec. 18, 2002, provisional application No. 60/434,452, filed on Dec. 18, 2002, provisional application No. 60/434,501, filed on Dec. 18, 2002, provisional application No. 60/461,164, filed on Apr. 8, 2003.

(51) Int. Cl.
*A61K 36/00* (2006.01)
*A61K 9/14* (2006.01)
*A61K 9/08* (2006.01)
*A61K 9/10* (2006.01)

(52) U.S. Cl.
USPC ......... 514/16.8; 514/18.4; 514/818; 424/489; 424/497

(58) Field of Classification Search .................. None
See application file for complete search history.

(56) References Cited

U.S. PATENT DOCUMENTS

| | | | | |
|---|---|---|---|---|
| 4,097,607 A * | 6/1978 | Larson | 514/627 |
| 4,313,958 A | 2/1982 | LaHann | 514/627 |
| 4,401,663 A | 8/1983 | Buckwalter et al. | 514/605 |
| 4,424,205 A | 1/1984 | LaHann et al. | 8/161 |
| 4,443,473 A | 4/1984 | Buckwalter et al. | 514/487 |
| 4,460,602 A | 7/1984 | Buckwalter et al. | 514/557 |
| 4,486,450 A | 12/1984 | Bernstein | 514/627 |
| 4,493,848 A | 1/1985 | LaHann et al. | 514/627 |
| 4,536,404 A | 8/1985 | Bernstein | 514/627 |
| 4,599,342 A | 7/1986 | LaHann | 514/282 |
| 4,681,897 A | 7/1987 | Brand | 514/557 |
| 4,702,916 A | 10/1987 | Geria | 424/400 |
| 4,742,054 A | 5/1988 | Naftchi | 514/215 |
| 4,801,587 A | 1/1989 | Voss et al. | 514/248 |
| 4,812,446 A | 3/1989 | Brand | 514/165 |
| 4,939,149 A | 7/1990 | Blumberg | 514/691 |
| 4,997,853 A | 3/1991 | Bernstein | 514/626 |
| 5,008,289 A | 4/1991 | Bernstein | 514/535 |
| 5,021,450 A | 6/1991 | Blumberg | 514/453 |
| 5,063,060 A | 11/1991 | Bernstein | 424/422 |
| 5,094,782 A | 3/1992 | Chen et al. | 554/63 |
| 5,178,879 A | 1/1993 | Adekunle et al. | |
| 5,188,837 A * | 2/1993 | Domb | 424/450 |
| 5,242,944 A * | 9/1993 | Park et al. | 514/466 |
| 5,290,816 A | 3/1994 | Blumberg | 514/691 |
| 5,296,225 A | 3/1994 | Adekunle et al. | 424/760 |
| 5,431,914 A | 7/1995 | Adekunle et al. | 424/401 |
| 5,447,947 A | 9/1995 | Campbell | 514/392 |
| 5,560,910 A | 10/1996 | Crandall | 424/94.63 |
| 5,618,522 A * | 4/1997 | Kaleta et al. | 424/60 |
| 5,660,830 A | 8/1997 | Anderson | 424/760 |
| 5,665,378 A | 9/1997 | Davis et al. | 424/448 |
| 5,762,963 A | 6/1998 | Byas-Smith | 424/472 |
| 5,788,982 A | 8/1998 | Nadoolman et al. | 424/440 |
| 5,827,886 A | 10/1998 | Hersh | 514/562 |
| 5,854,291 A | 12/1998 | Laughlin et al. | 514/626 |
| 5,856,361 A | 1/1999 | Holt et al. | 514/627 |
| 5,869,533 A | 2/1999 | Holt | 514/627 |
| 5,874,420 A | 2/1999 | Pelleg | 514/81 |
| 5,885,597 A | 3/1999 | Botnecht et al. | 424/401 |
| 5,910,512 A | 6/1999 | Conant | 514/617 |
| 5,962,532 A | 10/1999 | Campbell et al. | 514/627 |
| 5,985,860 A | 11/1999 | Toppo | 514/159 |
| 5,994,407 A | 11/1999 | Cuilty-Siller | 514/627 |
| 6,060,060 A | 5/2000 | Belgorod | 424/760 |
| 6,063,381 A | 5/2000 | Staggs | 424/734 |
| 6,063,758 A | 5/2000 | Lappi et al. | 514/2 |

(Continued)

FOREIGN PATENT DOCUMENTS

| | | |
|---|---|---|
| CN | 1146353 | 4/1997 |
| EP | 0068590 (A1) | 1/1983 |

(Continued)

OTHER PUBLICATIONS

Brady. Baillieres Clin Rheumatol. Nov. 1997;11(4):749-68.*
Machner. Z Rheumatol 58:148-154 (1999).*
Lamer. Regional Anesthesia and Pain Medicine 24(4):347-351, 1999.*
Shavelson.Clin Podiatr Med Surg. Apr. 1992;9(2):349-63.*
Chow. Semin Musculoskelet Radiol. 1998;2(4):421-432.*
Crawford. J Bone Joint Surg Br. Mar. 1998;80(2):279-81.*
Machner Translation. Z Rheumatol 58:148-154 (1999).*
Reinhardt. Ophthalmologica. Jul.-Aug. 2002;216(4):256-60.*

(Continued)

*Primary Examiner* — David J Blanchard
*Assistant Examiner* — Lori K Mattison
(74) *Attorney, Agent, or Firm* — Pabst Patent Group LLP

(57) ABSTRACT

The present invention is directed to compositions and methods for relieving pain at a site in a human or animal by administering at a discrete site in a human or animal a dose of capsaicin in an amount effective to denervate the discrete site without eliciting an effect outside the discrete location.

28 Claims, 5 Drawing Sheets

U.S. PATENT DOCUMENTS

| | | | |
|---|---|---|---|
| 6,197,823 B1 | 3/2001 | Barr et al. | 514/627 |
| 6,201,014 B1 | 3/2001 | Gardiner | 514/463 |
| 6,201,022 B1 | 3/2001 | Mease et al. | 514/560 |
| 6,204,271 B1 | 3/2001 | Fairbanks et al. | 514/269 |
| 6,210,394 B1 | 4/2001 | Demopulos et al. | 604/512 |
| 6,221,915 B1 | 4/2001 | McCleane | 514/615 |
| 6,239,180 B1 | 5/2001 | Robbins | 514/627 |
| 6,248,345 B1 | 6/2001 | Goldenheim et al. | 424/449 |
| 6,248,744 B1 | 6/2001 | Eisenach | 514/256 |
| 6,248,788 B1 | 6/2001 | Robbins et al. | 514/627 |
| 6,277,386 B1 | 8/2001 | Kim et al. | 424/401 |
| 6,277,398 B1 | 8/2001 | Caruso | 424/443 |
| 6,284,797 B1 | 9/2001 | Rhodes | 514/627 |
| 6,326,020 B1 | 12/2001 | Kohane et al. | 424/426 |
| 6,368,618 B1 | 4/2002 | Jun et al. | 424/449 |
| 6,514,516 B1 * | 2/2003 | Chasin et al. | 424/426 |
| 6,632,839 B2 | 10/2003 | Neumann | 514/627 |
| 6,653,352 B2 | 11/2003 | Barr et al. | 514/627 |
| 2001/0033861 A1 * | 10/2001 | Lasic et al. | 424/450 |
| 2001/0034964 A1 | 11/2001 | Neumann | 43/132.1 |
| 2002/0086824 A1 * | 7/2002 | Warman et al. | 514/12 |
| 2003/0104085 A1 | 6/2003 | Yeomans | 424/760 |
| 2003/0203030 A1 | 10/2003 | Ashton et al. | 424/484 |
| 2004/0126430 A1 * | 7/2004 | Angel et al. | 424/487 |
| 2004/0156931 A1 | 8/2004 | Burch et al. | 424/760 |
| 2004/0161481 A1 | 8/2004 | Burch et al. | 424/760 |
| 2004/0186182 A1 | 9/2004 | Burch et al. | 514/625 |
| 2004/0191338 A1 | 9/2004 | Burch et al. | 424/760 |
| 2004/0204356 A1 | 10/2004 | Guenzler-Pukall et al. | 514/12 |
| 2004/0224037 A1 | 11/2004 | Romero-Mateo | 424/760 |
| 2005/0020690 A1 | 1/2005 | Burch et al. | 514/625 |
| 2005/0058734 A1 | 3/2005 | Burch et al. | 424/760 |
| 2005/0085652 A1 | 4/2005 | Chen et al. | 554/69 |
| 2006/0148903 A1 | 7/2006 | Burch et al. | |
| 2006/0269628 A1 | 11/2006 | Burch et al. | |

FOREIGN PATENT DOCUMENTS

| | | |
|---|---|---|
| EP | 0068592 (A1) | 1/1983 |
| EP | 0089710 (A1) | 9/1983 |
| EP | 0149545 (A2) | 7/1985 |
| EP | 0306060 (A2) | 3/1989 |
| EP | 1000618 (A1) | 5/2000 |
| EP | 1039802 (A1) | 10/2000 |
| EP | 1048294 (A2) | 11/2000 |
| EP | 0998288 (B1) | 6/2002 |
| GB | 2327041 | 1/1999 |
| JP | 2000247875 | 9/2000 |
| JP | 2000297036 | 10/2000 |
| JP | 2001158738 | 6/2001 |
| WO | 9014083 (A1) | 11/1990 |
| WO | 9640079 (A1) | 12/1996 |
| WO | 9820867 (A1) | 5/1998 |
| WO | 9840070 (A1) | 9/1998 |
| WO | WO 98/40070 * | 9/1998 |
| WO | 9851290 (A2) | 11/1998 |
| WO | 9853825 (A1) | 12/1998 |
| WO | 9930560 (A1) | 6/1999 |
| WO | 0045801 (A2) | 8/2000 |
| WO | 0050025 (A1) | 8/2000 |
| WO | 02007644 (A1) | 10/2002 |
| WO | 2004002202 (A2) | 3/2004 |

OTHER PUBLICATIONS

Hand. American Heritage Dictionary of the English Language.http://education.yahoo.com/reference/dictionary/entry/hand. Copyright 2009.*

Osteoarthritis Treatment. http://www.fauxpress.com/kimball/med/ortho/osteo/4.htm. Published Oct. 19, 2000.*

What is Osteoarthritis. http://www.fauxpress.com/kimball/med/ortho/osteo/1.htm. Published Jul. 23, 2001.*

Intra-articular. http://www.mondofacto.com/facts/dictionary?intra-articular. Published Mar. 5, 2000.*

Society for Neuroscience Abstracts vol. 18 part 1, Oct. 25-30, 1992; 22$^{nd}$ Annual Meeting 94.3-94.8.

Maggi., C.A., et al., "Similarities and differences in the action of resiniferatoxin and capsaicin on central and peripheral endings of primary sensory neurons", Neuroscience (1990) vol. 37 No. 2 pp. 532-539.

Dux, M., et al., "Inhibition of the neurogenic inflammatory response by lidocaine in rat skin", Inflamm Res (1996) vol. 45 pp. 10-13.

Wallengren, J. and Hakanson, R., "Effects of capsaicin, bradykinin and prostaglandin E-2 in the human skin", Brit J Derm (1992) vol. 126 pp. 111-117.

Lazzeri, M., et al., "Intravesical capsaicin for treatment of severe bladder pain: A randomized placebo controlled study", J Urol (1996) vol. 156 pp. 947-952.

Craft, R. and Porreca, F., "Tetracaine attenuates irritancy without attenuating desensitization produced by intravesical resiniferatoxin in the rat", Pain (1994) vol. 57 pp. 351-359.

Winning, A.J., et al., "Respiratory and cardiovascular effects of central and peripheral intravenous injections of capsaicin in man: evidence for pulmonary chemosensitivity", Clinical Science (1986) vol. 71 pp. 519-526.

Schneider, M., et al., "A preferential inhibition of impulses in C-fibers of the rabbit vagus nerve by veratridine, an activator of sodium channels", Anesth(1991) vol. 74 p. 270-280.

Toh, C.C., et al., "The pharmacological actions of capsaicin and analogues", Brit J. Pharmacol (1955) vol. 10 pp. 175-182.

Davis, K.D., et al.,"Cutaneous injection of the capsaicin analogue, NE-21610, produces analgesia to heat but not to mechanical stimuli in man", Pain (1995) vol. 61 pp. 17-26.

Davis, K.D., et al."Cutaneous pretreatment with the capsaicin analogue, NE-21610, prevents the pain to a burn and subsequent hyperalgesia", Pain (1995) vol. 62 pp. 373-378.

Epstein, J.B., "Topical application of capsaicin for treatment of oral neuropathic pain and trigeminal neuralgia", Oral Surg Oral Med Oral Path (1994) vol. 77 pp. 135-140.

Haynes, D.H. and Kirkpatrick, A.F., "Ultra-long duration local anesthesia produced by injection of lecithin-coated methoxyfurane microdroplets", Anesth (1985) vol. 63 pp. 490-499.

Bessou, P. and Perl, E.R., "Response of the cutaneous sensory units with unmyelinated fibers to noxious stimuli", J Neurophysiol (1969) vol. 32 pp. 1025-1043.

Carpenter, S.E. and Lynn, B., "Vascular and Sensory responses of human skin to mild injury after topical treatment with capsaicin", Brit J Pharmacol (1981) vol. 73 pp. 755-758.

Carter, R.B., "Topical capsaicin in the treatment of cutaneous disorders", Drug Dev Res (1991) vol. 22 pp. 109-123.

Caterina, M.J., et al., "The capsaicin receptor: a heat activated ion channel in the pain pathway", Nature (1997) vol. 389 pp. 816-824.

Caterina, M.J. and Julius, D., "The vanilloid receptor: a molecular gateway to the pain pathway", Annu Rev Neuroscience (2001) vol. 24 pp. 487-517.

Dasgupta, P., et al.,"Treating the human bladder with capsaicin: is it safe?", Eur Urol (1998) vol. 33 pp. 28-31.

deSeze, M., et al., "Reiterated intravesical instillation of capsaicin in neurogenic detrusor hyperrefelxia: a 5-years experience of 100 instillations", Ann Reapt Med Phys (2001) vol. 44 pp. 514-524.

Desjardins, P.J., et al., "A single preoperative oral dose of Valdecoxib, a new cyclo-oxygenase-2 specific inhibitor, relives post-oral surgery or bunionectomy pain", Anesth (2002) vol. 97 No. 3 pp. 189-203.

Dirks, J., et al., "The effect of systemic lidocaine on pain and secondary hyperalgesia associated with the heat/capsaicin sensitization model in healthy volunteers", Anesth Analg (2000) vol. 91 pp. 967-972.

Hiura, A., et al., "Age-dependent attenuation of the decrease of C fibers by capsaicin and its effects on responses to nociceptive stimuli", Somatosens Mot Res (1992) vol. 9 pp. 37-43.

Holzer, P., "Capsaicin: cellular targets, mechanisms of action, and selectivity for thin sensory neurons", Pharmacol Rev (1991) vol. 43 pp. 143-201.

Jancso, N., et al., Direct evidence for neurogenic inflammation and its prevention by denervation and by pretreatment with capsaicin, Brti J Pharmacol (1967) vol. 31 pp. 138-151.

Jancso, N., et al., "The role of sensory nerve endings in neurogenic inflammation induced in human skin and in the eye and paw of the rat", Brit J Pharmacol (1968) vol. 33 pp. 32-41.

Jancso, G., et al., "Pharmacologically induced selective degeneration of chemosensitive primary sensory neurons", Nature (1977) vol. 270 pp. 741-743.

Jancso, G., et al., "The modulation of cutaneous inflammatory reactions by peptide-containing sensory nerves", Intl J Tissue React (1985) vol. 7 pp. 449-457.

Joo, F., et al., "Mitochondrial alterations in the spinal ganglion cells of the rat accompanying the long-lasting sensory disturbance induced by capsaicin", Life Sci (1969) vol. 8 pp. 621-626.

Kenins, P., "Responses of single nerve fibers to capsaicin applied to the skin", Neurosci Lett (1982) vol. 29 pp. 83-88.

Koppert, W., et al., "Low-dose lidocaine reduces secondary hyperalgesia by a central mode of action", Pain (2000) vol. 85 pp. 217-224.

Lam, F.Y. and Ferrell, W.R., "Inhibition of carrageenan induced inflammation in the rat knee joint by substance P antagonist", Ann Rheum Dis (1989) vol. 48 pp. 928-932.

Lam, F.Y. and Ferrell, W.R., "Neurogenic component of different models of acute inflammation in the rat knee joint", Ann Rheum Dis (1991) vol. 50 pp. 747-751.

Lamotte, R.H. and Campbell, J.N., "Comparison of responses of warm and nociceptive C-fiber afferents in monkey with human judgements of thermal pain", J Neurophysiol (1978) vol. 41 pp. 509-528.

Lamotte, R.H., et al., "Neurogenic hyperalgesia: psychophysical studies of underlying mechanisms", J Neurophysiol (1991) vol. 66 pp. 190-211.

Lynn, B. and Carpenter, S.E., "Primary afferent units from the hairy skin of the rat hind limb", Brain Res (1982) vol. 238 pp. 29-43.

Lynn, B. "Capsaicin: actions on nociceptive C-fibers and therapeutic potential", Pain (1990) vol. 41 pp. 61-69.

Lynn, B., et al., "The actions of capsaicin applied topically to the skin of the rat on C-fibre afferents, antidromic vasodilation and substance P levels", Brit J Pharmacol (1992) vol. 107 pp. 400-406.

Nolano, M., et al., "Topical capsaicin in humans: parallel loss of epidermal nerve fibers and pain sensation", Pain (1999) vol. 81 pp. 135-145.

Simone, D.A., et al., "Dose-dependent pain and mechanical hyperalgesia in humans after intradermal injection of capsaicin", Pain (1989) vol. 38 pp. 99-107.

Szallasi, A., et al., "The cloned rat vanilloid receptor VR1 mediates both R-type binding and C-type calcium response in dorsal root ganglion neurons", Mol Pharmacol (1999) vol. 56 pp. 581-587.

Szolcsanyi, J., "A pharmacological approach to elucidation of the role of different nerve fibers and receptor endings in mediation of pain", J Physiol (1977) vol. 73 pp. 251-259.

Szolcsanyi, J., "Selective responsiveness of polymodal nociceptors of the rabbit ear to capsaicin, bradykinin and ultra-violet irradiation", J Physiol (1987) vol. 288 pp. 9-23.

Szolcsanyi, J., "Actions of capsaicin on sensory receptors", Capsaicin in the Study of Pain, Academic Press (1993) pp. 1-26.

Tominaga, M., et al., "The cloned capsaicin receptor integrates multiple pain-producing stimuli", Neuron (1998) vol. 21 pp. 531-543.

Cha, B., et al., "Enhanced skin permeation of a new capsaicin derivative (DA-5018) from a binary vehicle system composed of isopropyl myristate and ethoxydiglycol", Arch Pharm Res (2001) vol. 24 pp. 224-228.

Jung, J., et al., "Capsaicin binds to the intracellular domain of the capsaicin-activated ion channel", J Neurosci (1999) vol. 19 pp. 529-538.

Kang, Y.S. and Kim, J.M., "Permeability of capsaicin derivative, [14C]DA-5018 to blood-brain barrier corrected with HPLC method", Arch Pharm Res (1999) vol. 22 pp. 165-172.

O'Hollaren, M.T., and Porter, G.A., "Angiotensin converting enzyme inhibitors and the allergist", Annals Allergy (1990) vol. 64 pp. 503-504.

Max, M.B., et al., "Efficacy of desipramine in painful diabetic neuropathy: a placebo-controlled trial", Pain (1991) vol. 45 pp. 3-9.

Kim, D.H., et al., "Antipuritic effect of DA-5018, a capsaicin derivative, in mice", Arch Pharm Res (1999) vol. 22 pp. 549-553.

Lee, J.J., et al., "Pharmacokinetics of non-narcotic analgesic, DA-5018, in rats", Biopharm Drug Dispos (1998) vol. 19 pp. 101-108.

Park, N.S. et al., "The Crystal Structure of KR-21042; An Analgesic Capsaicinoid", Arch Pharm Res (2002) vol. 25, No. 1, pp. 25-27.

Shim, H.J., et al.,"Determination of a new non-narcotic analgesic, DA-5018, in plasma, urine and bile by high-performance liquid chromatography", J Chromatogr B Biomed Sci Appl (1997) vol. 689 pp. 422-426.

Shim, H.J., et al. "Stability, blood partition, and protein binding of DA-5018, a new non-narcotic analgesic", Res Commun Mol Pathol Pharmacol (1996) vol. 91 pp. 97-108.

Shin, J.S., "Differences in sensitivity of vanilloid receptor 1 transfected to human embryonic kidney cells and capsaicin-activated channels in cultured rat dorsal ganglion neurons to capsaicin receptor agonists", Neurosci Lett (2001) vol. 299 pp. 135-139.

Sim, J.H., et al., "Capsaicin inhibits the voltage-operated calcium channels intracellularly in the antral circular myocytes of the guinea-pig stomach", Life Sci (2001) vol. 68 pp. 2347-2360.

Ko, M. and Woods, J.H., "Local administration of $\Delta^9$-tetrahydrocannabinol attenuates capsaicin-induced thermal nociception in rhesus monkeys: A peripheral cannabinoid action", Psychopharmacol (1999) vol. 143 No. 3 pp. 322-326.

Ko, M.C., et al., "Local administration of mu or kappa opioid agonists attenuates capsaicin-induced thermal hyperalgesia via peripheral opioid receptors in rats", Psychopharmacol (2000) vol. 148 No. 2 pp. 180-185.

Koppert, W., et al., "The effects of intradermal fentanyl and ketamine on capsaicin-induced secondary hyperalgesia and flare reaction", Anesth Analg (1999) vol. 89 No. 6 pp. 1521-1527.

Treede, R.D., et al,"Evidence that peripheral α-adrenergic receptors mediate sympathetically maintained pain", Proceedings of the $6^{th}$ World Congress on Pain (1991) pp. 373-378.

Janig, W., "Causalgia and reflex sympathetic dystrophy: in which way is the sympathetic nervous system involved?", Tins (Nov. 1985) pp. 471-477.

Martindale, The Extra Pharmacopoeia, $28^{th}$ ed., Reynolds, James E.F., editor (1982) pp. 139-141.

Kohane, D.S., et al., "Vanilloid receptor agonists potentiate the in vivo local anesthetic activity of percutaneously injected site 1 sodium channel blockers", Anesth (1999) vol. 90 No. 2 pp. 524-534.

Serra, J., et al., "Flare and hyperalgesia after intradermal capsaicin injection in human skin", J Neurophysiol (1998) vol. 80 No. 6 pp. 2801-2810.

Kalman, et al., "Differential effect on vasodilation and pain after intradermal capsaicin in humans during decay of intravenous regional anesthesia with mepivacaine", Reg Anesth Pain Med (1998) vol. 23 No. 4 pp. 402-408.

Burger's Medicinal Chemistry, $4^{th}$ Ed Pt 3, Wolf, Manfred, E., editor (1981) pp. 285-310 & 931-934.

Goodman & Gilman's The Pharmacological Basis of Therapeutics, $8^{th}$ Ed., Gilman, A.G., et al., editor (1990) pp. 221-236 & 788-799.

Goodman & Gilman's The Pharmacological Basis of Therapeutics, $6^{th}$ Ed., Gilman, A.G., et al., editor (1980) pp. 197-210.

Katzung, B., "Introduction to Autonomic Pharmacology", Basic and Clinical Pharmacology, Chpt 6. McGraw-Hill, publisher (2000) pp. 69-81.

Bernstein, J.E., et al., "Topical capsaicin treatment of chronic postherpetic neuralgia", J Amer Acad Derm pp. 267-268.

Robertson, D.R.C. and George, C.F., "Treatment of post herpetic neuralgia in the elderly", Brit Med Bull (1990) vol. 46 No. 1 pp. 113-123.

Inman, R.D., et al., "Neuromodulation of synovitis: capsaicin effect on severity of experimental arthritis", J Neuroimmunol (1989) vol. 24 pp. 17-22.

Lam, F.Y. and Ferrell, W.R., "Capsaicin suppresses substance P-induced joint inflammation in the rat", Neurosci Lett (1989) vol. 105 pp. 155-158.

Mapp, P.I., et al., "The effect of intra-articular capsaicin on nerve fibers within the synovium of the rat knee joint", J Chem Neuroanat (1996) vol. 10 pp. 11-18.

Marshall, K.W., et al., "A single capsaicin injection partially depletes neuropeptides but does not ameliorate inflammation severity in established feline antigen induced arthritis", J Rheumatol (1997) vol. 24 pp. 1765-1768.

Yaksh, T.L., "Substance P release from knee joint afferent terminals: modulation by opioids", Brain Res (1988) vol. 458 pp. 319-324.

Szallasi, A. and DiMarzo, V., "New Perspectives on enigmatic vanilloid receptors", Tins (2000) vol. 23 No. 10 pp. 491-497.

Szallasi, A. and Sterner, O., "Novel natural vaniloid receptor agonists: new therapeutic targets for drug development", TiPS (1999) vol. 20 pp. 459-465.

Park, N.S., "KR-25003, a potent analgesic capsaicinoid", Acta Crystallogr C (1995) vol. 51, Pt 5 pp. 927-929.

Hussain et al. "Chemical activation of thin-fiber phrenic afferents: respiratory responses" J. Appl. Physiol. (1985) vol. 69, No. 3, pp. 1002-1011.

Dib, B. "Dissociation Between Peripheral and Central Heat Loss Mechanisms Induced by Neonatal Capsaicin" Behavioral Neurosc. (1983) vol. 97, No. 5, pp. 822-825.

Szolcsanyi et al. "Nociception in pigeons is not impaired by capsaicin" Pain (1986) vol. 27, No. 2, pp. 247-260.

Selvaggio, M et al, "Potentiation of the anagesic effect of naproxen by capsaicin in the mouse abdominal constriction model of visceral pain", European Journal of Pharmaceutical Sciences, vol. 6, No. Suppl 1, 1998 p. S58.

Altman, et al., "Capsaicin cream 0.025% as monotherapy for osteoarthritis: A double-blind study", Seminars in Arthritis and Rheumatism, 23(6):25-33 (1994).

Schnitzer, et al., "Topical capsaicin therapy for osteoarthritis pain: achieving a maintenance regimen", Seminars in Arthritis and Rheumatism, 23(6):34-40 (1994).

* cited by examiner

Change in NRS pain score at three weeks following administration, P = 0.05
Final NRS score, placebo = 7.30, ALGRX 4975 = 3.97, P = 0.03

INJECTABLE CAPSAICIN

This application is a Divisional application of U.S. Ser. No. 10/742,621, filed Dec. 18, 2003, now abandoned, which claims the benefit of U.S. Provisional Patent Application No. 60/434,453, filed Dec. 18, 2002, U.S. Provisional Patent Application No. 60/434,530, filed Dec. 18, 2002, U.S. Provisional Patent Application No. 60/434,500, filed Dec. 18, 2002, U.S. Provisional Patent Application No. 60/434,828, filed Dec. 18, 2002, U.S. Provisional Patent Application No. 60/434,452, filed Dec. 18, 2002, U.S. Provisional Patent Application No. 60/434,501, filed Dec. 18, 2002, and U.S. Provisional Patent Application No. 60/461,164, filed Apr. 8, 2003, the disclosures of which is hereby incorporated by reference in their entirety.

FIELD OF THE INVENTION

This application is directed to compositions and methods for relieving pain at a specific site, for example, associated with inflammation of joints, tendons, nerves, muscle, and other soft tissues, nerve injury and neuropathies, and pain from tumors in soft tissues or bone.

BACKGROUND OF THE INVENTION

Capsaicin, a pungent substance derived from the plants of the solanaceae family (hot chili peppers) has long been used as an experimental tool because of its selective action on the small diameter afferent nerve fibers C-fibers and A-delta fibers that are believed to signal pain. From studies in animals, capsaicin appears to trigger C-fiber membrane depolarization by opening cation channels permeable to calcium and sodium. Recently one of the receptors for capsaicin effects has been cloned. Capsaicin can be readily obtained by ethanol extraction of the fruit of *capsicum frutescens* or *capsicum annum*. Capsaicin is known by the chemical name N-(4-hydroxy-3-methoxybenzyl)-8-methylnon-trans-6-enamide. Capsaicin is practically insoluble in water, but freely soluble in alcohol, ether, benzene and chloroform. Therapeutically capsaicin has been used as a topical analgesic. Capsaicin is available commercially as Capsaicin USP from Steve Weiss & Co., 315 East 68$^{th}$ Street, New York, N.Y. 10021 and can also be prepared synthetically by published methods. See Michalska et al., "Synthesis and Local Anesthetic Properties of N-substituted 3,4-Dimethoxyphenethylamine Derivatives", Diss Pharm. Pharmacol., Vol. 24, (1972), pp. 17-25, (Chem. Abs. 77: 19271a), discloses N-pentyl and N-hexyl 3,4-dimethoxyphenylacetamides which are reduced to the respective secondary amines.

Capsaicin is listed in the pharmacopoeias of the United Kingdom, Australia, Belgium, Egypt, Germany, Hungary, Italy, Japan, Poland, Portugal, Spain, and Switzerland and has previously been listed in the United States Pharmacopoeia and the National Formulary. The FDA proposed monographs on analgesic drug products for over-the-counter (OTC) human use. These include capsaicin and *capsicum* preparations that are regarded as safe and effective for use as OTC external analgesics. Capsaicin is the only chemical entity of *Capsicum* recognized by the FDA. Capsaicin (USP) contains not less than 110% total capsaicinoids which typically corresponds to 63% pure capsaicin. USP capsaicin is trans-capsaicin (55-60%) and also contains the precursors dihydrocapsaicin and nordihydrocapsaicin.

Capsaicin mediated effects include: (i) activation of nociceptors in peripheral tissues; (ii) eventual desensitization of peripheral nociceptors to one or more stimulus modalities; (iii) cellular degeneration of sensitive A-delta and C-fiber afferents; (iv) activation of neuronal proteases; (v) blockage of axonal transport; and (vi) the decrease of the absolute number of nociceptive fibers without affecting the number of non-nociceptive fibers.

The dosage forms of capsaicin which have been most widely studied clinically are capsaicin containing creams (Zostrix, Zostrix-HP, and Axsain). These products have been examined in a broad spectrum of painful conditions including osteoarthritis. However the efficacy of topically administered capsaicin in arthritis in general has proven to be limited.

Prior publications describe topical administration of capsaicin for the treatment of various conditions. For example, U.S. Pat. No. 4,997,853 (Bernstein) describes methods and compositions utilizing capsaicin as an external analgesic. U.S. Pat. No. 5,063,060 (Bernstein) describes compositions and methods for treating painful, inflammatory or allergic disorders. U.S. Pat. No. 5,178,879 (Adekunle, et al.) describes methods for preparing a non-greasy capsaicin gel for topical administration for the treatment of pain. U.S. Pat. No. 5,296,225 (Adekunle, et al.) describes indirect methods of treating orofacial pain with topical capsaicin. U.S. Pat. No. 5,665,378 (Davis, et al.) describes transdermal therapeutic formulations comprising capsaicin, a nonsteroidal anti-inflammatory agent and pamabrom for the treatment of pain. U.S. Pat. No. 6,248,788 (Robbins, et al.) describes administration of 7.5% capsaicin cream in combination with marcaine epidural injections in patients suffering from long-term persistent foot pain. U.S. Pat. No. 6,239,180 (Robbins) describes combining capsaicin loaded patches with local anesthesia to treat peripheral neuropathy. The use of topical capsaicin has also been described in the art to treat conditions as diverse as post mastectomy pain syndrome (Watson and Evans, Pain 51: 375-79 (1992)); painful diabetic neuropathy (Tandan et al., Diabetes Care 15: 8-13 (1992)); The Capsaicin Study Group, Arch Intern Med 151: 2225-9 (1991); post-herpetic neuralgia (Watson et al., Pain 33: 333-40 (1988)), Watson et al., Clin. Ther. 15: 510-26 (1993); Bernstein et al., J. Am Acad Dermatol 21: 265-70 (1989) and pain in Guillian-Barre syndrome (Morganlander et al., Annals of Neurology 29:199 (1990)). Capsaicin has also been used in the treatment of osteoarthritis (Deal et al., Clin Ther 13: 383-95 (1991); McCarthy and McCarthy, J. Rheumatol 19: 604-7 (1992); Altman et al., Seminars in Arthritis and Rheumatism 23: 25-33 (1994). In addition, U.S. Pat. No. 4,599,342 (LaHann) describes oral and subcutaneous or intramuscular administration of a combination of capsaicin or a capsaicin analog with an opioid analgesic. U.S. Pat. No. 4,313,958 (LaHann) describes intrathecal, epidural, intramuscular, intravenous, intraperitoneal and subcutaneous administration of capsaicin utilizing a "stair-step" dosing pattern.

Humans have long been exposed to dietary sources of capsaicin-containing spices and to topical preparations used for a variety of medical indications. This vast experience has not revealed significant or lasting adverse effects of capsaicin exposure. The recent determination of capsaicin's potential therapeutic effects on unmyelinated sensory afferent nerve fibers require diligent consideration of this compound for further pharmaceutical development.

Because of the ability of capsaicin to desensitize nociceptors in peripheral tissues, its potential analgesic effects have also been assessed in various clinical trials. However, since the application of capsaicin itself frequently causes burning pain and hyperalgesia apart from the neuropathic pain being treated, patient compliance has been poor and the drop out rates during clinical trials have exceeded fifty percent. The spontaneous burning pain and hyperalgesia are believed to be due to intense activation and temporary sensitization of the peripheral nociceptors at the site of capsaicin application. This activation and sensitization occur prior to the desensitization phase. The activation phase could be a barrier to use of capsaicin because of the pain produced.

It would therefore be advantageous to provide methods and compositions including capsaicin or capsaicin analogues thereof with effective concentrations to cause an analgesic effect without the side effects normally associated with the use of capsaicin.

OBJECTS AND SUMMARY OF THE INVENTION

It is an object of the present invention to provide compositions and methods for providing pain relief in humans and animals by administering an injectable or implantable dose of capsaicin or capsaicin analogue to a site for the treatment of acute or chronic pain, nociceptive and neuropathic pain, pre- and post-operative pain, cancer pain, pain associated with neurotransmitter dysregulation syndromes and orthopedic disorders.

It is another object of the invention to provide compositions and methods for attenuating pain at a discrete site in a human or animal via the administration of a capsaicinoid via injection or implantation at the discrete site.

It is another object of the present invention to provide compositions and methods for relieving pain at an intra-articular site or at a body space by administering an injectable or implantable single dose of capsaicin or capsaicin analogue to the intra-articular site or body space.

It is a further object of the invention to provide compositions and methods for treatment of sports-related injuries utilizing injectable or implantable capsaicinoids.

It is a further object of the invention to provide compositions and methods for treatment of orthopaedic disorders or injuries utilizing injectable or implantable capsaicinoids.

It is a further object of the invention to provide compositions and methods for treating acute traumatic pain utilizing injectable or implantable capsaicinoids.

It is a further object of the invention to provide compositions and methods for treating neuropathic pain utilizing injectable or implantable capsaicinoids.

It is a further object of the invention to provide compositions and methods for treating nociceptive pain utilizing injectable or implantable capsaicinoids.

It is a further object of the invention to provide compositions and methods for treating neurotransmitter-dysregulation syndromes utilizing injectable or implantable capsaicinoids.

In accordance with the above objects and others, in certain embodiments of the present invention, there is provided a method for attenuating or relieving pain at a site in a human or animal in need thereof, comprising administering via injection or implantation at a discrete site in a human or animal in need thereof a dose of capsaicin in an amount effective to denervate the discrete site without eliciting an effect outside the discrete location and to attenuate pain emanating from said site, the dose ranging from about 1 µg to about 5,000 µg capsaicin or a therapeutically equivalent dose of a capsaicinoid other than capsaicin. In other words, the term "capsaicinoid" is meant to encompass formulations where the drug is capsaicin, a capsaicinoid other than capsaicin, or a mixture of capsaicin with one or more other capsaicinoids (the total amount of all capsaicinoid drug being based on a therapeutically equivalent dose to dose from about 1 µg to about 5,000 µg capsaicin).

In certain preferred embodiments of the present invention, the dose of capsaicinoid contained in a unit dose injection/implantation is from about 1 µg to about 5000 µg of capsaicin, preferably from about 10 µg to about 3000 µg capsaicin, more preferably from about 300 µg to about 1500 µg capsaicin, or a therapeutically equivalent amount of one or more capsaicinoids. In certain preferred embodiments, the dose of capsaicin is from about 400 µg to about 1200 µg, or a therapeutically equivalent amount of one or more capsaicinoids. In certain other embodiments, the dose of capsaicin is preferably from about 10 µg to about 1000 µg, more preferably from about 20 µg to about 300 µg, and most preferably from about 35 µg to about 200 µg. Preferably, the capsaicinoid is administered in a pharmaceutically and physiologically acceptable vehicle for injection or implantation, which may optionally further include one or more additional pharmaceutical excipients.

The dose of capsacinoid may be injected or implanted subcutaneously, intramuscularly, itrathecally, epidurally, intraperitoneally, caudally intradermally or intracutaneously, intercostally at a single nerve, intra-articularly, intrasynovially, intraspinally, intra-arterially or into body spaces. Intra-articular administration of the formulations of the invention may be, e.g., into a joint selected from the group consisting of knee, elbow, hip, sternoclavicular, temporomandibular, carpal, tarsal, wrist, ankle, intervertebral disk, ligamentum flavum and any other joint subject to pain.

In certain preferred embodiments, a local anesthetic may be administered prior to or concurrently with said dose of capsaicinoid in an amount and location effective to attenuate an initial hyperalgesic effect of the administered dose of capsaicinoid. The local anesthetic may be administered, e.g., by direct injection into the site where said dose of capsaicinoid is administered, or as a proximal, regional, somatic, or neuraxial block. General anesthesia may be used, if necessary.

In certain embodiments, the administration of capsaicinoid at the discrete site provides pain attenuation or pain relief for at least about 48 hours to about 16 weeks.

The invention is further directed in part to a method of treating acute traumatic pain associated with an injury, comprising injecting a capsaicinoid in a physiologically compatible vehicle through the skin of a patient in proximity to an injury, said dose of capsaicinoid being sufficient to attenuate the dull, aching pain associated with C-fibers in proximity to the injury and such that the patient continues to have sensation in proximity to the injury and without affecting sharp protective pain associated with A-delta fibers in proximity to the site, the dose of capsaicinoid being therapeutically equivalent to a dose of capsaicin in an amount from about 300 to about 1500 µg and being effective to attenuate dull, aching pain in proximity to the injury for at least about 48 hours.

In certain preferred embodiments, the capsaicinoid is capsaicin itself. In more preferred embodiments, the capsaicinoid comprises trans-capsaicin. In most preferred embodiments, the capsaicinoid is at least about 97% trans-capsaicin.

The single injectable or implantable dose of a capsaicinoid administered at a discrete painful site in accordance with the present invention is preferably in an amount effective to a) produce a selective, highly-localized destruction or incapacitation of C-fibers and/or A-delta fibers in a discrete, localized area responsible for the initiation of pain for the purpose of reducing or eliminating pain arising from a discrete locus, and b) minimize potential adverse consequences of C-fiber and/or A-delta activation and or damage outside of the locus of pain.

The present invention is also directed to an injectable or implantable pharmaceutical composition for attenuating pain at a site in a human or animal in need thereof, consisting essentially of from 1 µg to 5000 µg of a capsaicinoid comprising trans-capsaicin and a pharmaceutically acceptable vehicle for injection or implantation. In certain preferred embodiments, the dose of trans-capsaicin ranges from about 10 µg to about 3000 µg, from about 300 µg to about 1500 µg, or preferably from about 400 µg to about 1200 µg.

In order that the invention described herein may be more fully understood, the following definitions are provided for the purposes of this disclosure:

The term "injection" shall mean administration of capsaicin to a discrete site through the skin of a human or animal.

The term "implantation" shall mean administration of capsaicin to a discrete site by embedding the dose of capsaicin into the skin, tissue, muscles, tendons, joints, or other body parts of a human or animal.

The term "infiltration" shall mean administration into a discrete surgical site where the surgical wound is open.

As used herein, the term "capsaicinoid" means capsaicin, capsaicin USP and purified capsaicin, capsaicin analogues and derivatives thereof (collectively referred to as capsaicinoids in this specification and appended claims) that act at the same pharmacologic sites, e.g., VR1, as capsaicin, unless otherwise specified.

Acute pain shall mean any pain that presents with a rapid onset followed by a short, severe course, e.g., headache, pain associated with cancer, fractures, strains, sprains, and dislocations of bones, joints, ligaments and tendons.

Chronic pain shall mean pain that lasts for a long period of time or is marked by frequent recurrence, e.g., pain associated with terminal illnesses, arthritis, autoimmune diseases; or neuropathic pain caused by degenerative diseases such as diabetes mellitus or spinal degeneration, or resulting from neural remodeling following traumatic injury or surgery.

As used herein, the term "local anesthetic" means any drug or mixture of drugs that provides local numbness and/or analgesia.

By co-administration it is meant either the administration of a single composition containing both the capsaicin and an additional therapeutically effective agent(s), e.g., local anesthetic or phenol, or the administration of a capsaicin and the additional therapeutically effective agent(s) as separate compositions within short enough time periods that the effective result is equivalent to that obtained when both compounds are administered as a single composition.

BRIEF DESCRIPTION OF THE DRAWINGS

The following drawings are illustrative of embodiments of the invention and are not meant to limit the scope of the invention as encompassed by the claims.

DETAILED DESCRIPTION OF THE INVENTION

Figure 1:
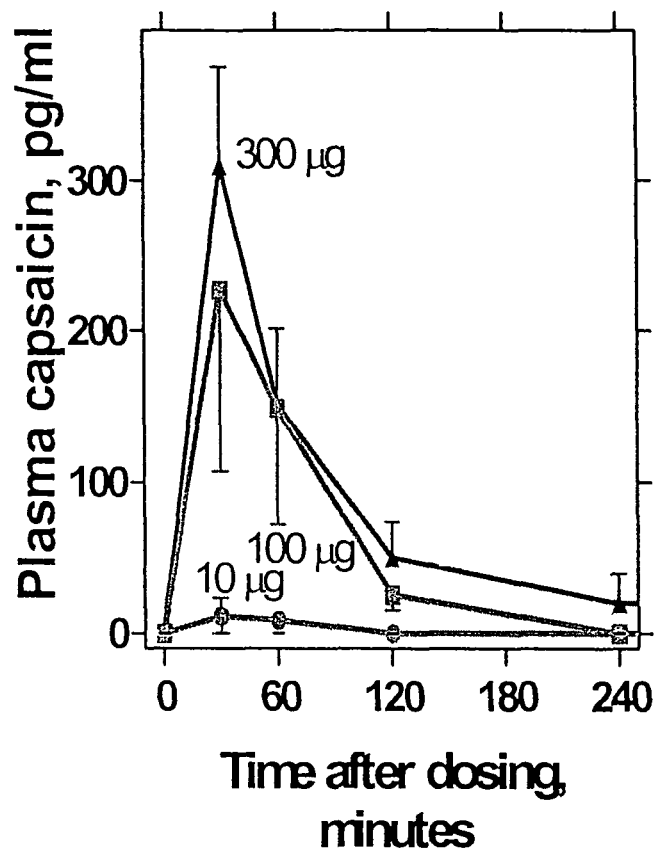
FIG. 1 is a graph displaying the plasma concentration of the 10 µg, 100 µg and 300 µg doses of capsaicin administered to study subjects entered into the Osteoarthritis Safety Study exemplified in Example 1.

The compositions and methods disclosed herein can be used for treating pain at a specific site with an effective amount of capsaicin or capsaicin analogue, hereinafter collectively referred to as "capsaicinoids". In one preferred embodiment, the methods involve administration of an effective amount of capsaicinoid to a discrete site in a human or animal for relieving pain at the site.

In another embodiment, the methods involve providing anesthesia to the site where the capsaicinoid is to be administered, and then administering an effective amount of capsaicinoid to the site to attenuate the pain emanating from the site, e.g., for at least about 72 hours. The anesthesia can be provided directly to the site, or at a remote site that causes anesthesia at the site where the capsaicinoid is to be administered. For example, epidural regional anesthesia can be provided to patients to which the capsaicinoid is to be administered at a site located from the waist down. Alternatively, a local anesthetic may be administered as a regional block, a proximal block, a somatic block, or a neuraxial block. The anesthetic may be administered as a general anesthetic, as a spinal block, as an epidural block, or as a nerve block. Preferably, in the embodiments in which a local anesthetic is administered, the local anesthetic is administered prior to administration of the capsaicinoid, such that the local anesthetic has provided temporary anesthesia to the area to be treated with the capsaicinoid.

Examples of local anesthetic agents which can be used include bupivacaine, ropivacaine, dibucaine, procaine, chloroprocaine, prilocalne, mepivacaine, etidocaine, tetracaine, lidocaine, and xylocaine, and mixtures thereof and any other art-known pharmaceutically acceptable local anesthetic. The local anesthetic can be in the form of a salt, for example, the hydrochloride, bromide, acetate, citrate, carbonate or sulfate. In certain embodiments, the local anesthetic agent is in the form of a free base. Preferred local anesthetic agents include, e.g., bupivacaine or lidocaine. For bupivacaine, the free base provides a slower initial release and avoids an early "dumping" of the local anesthetic at the injection site. Other local anesthetics may act differently. Local anesthetic agents typically administered systematically may also be used in those cases where the means of administration results only in a local effect, rather than systemic.

The dose of local anesthetic will depend on the anesthetic being administered as well as the site where the local anesthetic is administered. For example, in embodiments where the local anesthetic is administered via a regional block (e.g., an ankle block), the dose of anesthetic ranges from about 1 ml up to about 30 ml of a 0.5% solution (e.g., bupivacaine). In other embodiments a 3 mg/kg dose (maximum 200 mg) of a 2% solution (e.g., lidocaine) can be administered by intr-articular infiltration. In other embodiments the dose of local anesthetic can range between 0.5 ml to about 60 ml of a 0.25% to 5% solution.

Alternatively, phenol can be administered at the site to be treated in place of (or in addition to) a local anesthetic to anesthesize the area. Phenol can preferably be administered prior to administration of the capsaicinoid, or can be co-administered with the dose of capsaicinoid. By co-administration it is meant either the administration of a single composition containing both the capsaicinoid and the phenol, or the administration of the capsaicinoid and the phenol as separate compositions within short enough time periods that the effective result is equivalent to that obtained when both compounds are administered as a single composition.

Prior to the present invention, for example, in U.S. Pat. No. 4,313,958 (LaHann), capsaicin is described as producing analgesia when administered via "systemic administration" (i.e., intrathecal, epidural, intramuscular, intravenous, intraperitoneal and subcutaneous). Animal testing was accomplished via "stair-step dosing" which purportedly was said to reduce or eliminate some of the side affects of capsaicin. It is reported therein that capsaicin, when systemically delivered in final doses of 25 mg/kg or less prior to ultra violet radiation, prevented radiation induced hyperalgesia, but did not elevate the pain threshold above normal range. Only when larger doses of capsaicin were administered systemically, i.e. final doses of capsaicin being 50 mg/kg or greater, was the pain threshold elevated. LaHann hypothesized (but did not exemplify), that for clinical use in humans, total doses from 0.05 mg/kg to 1,000 mg/kg were acceptable and total doses from 0.25 mg/kg to 500 mg/kg were preferred. The rats weighed between 125 and 175 grams and the total administered dose of capsaicin ranged from 27 mg/kg to 102 mg/kg (or a total dose injected subcutaneously of about 3.375 mg to about 17.85 mg capsaicin).

More recently, U.S. Pat. No. 5,962,532 (Campbell et al) describes an injection volume of 0.1 to 20 ml and a concentration of capsaicin between 0.01 to 10% for parenteral administration, which calculates to a total dose of capsaicin of between 0.01 mg to 2,000 mg, based on volume and concentration.

In contrast, in the present invention, the administration of microgram quantities of capsaicin into discrete localized areas responsible for the treatment and/or attenuation of pain recognizes significant advantages over system-wide exposure to milligram quantities in order to produce a therapeutic effect through alteration of sensory nerve function in a limited area.

In the present invention, a single dose from about 1 µg to 5,000 µg of capsaicin, or a therapeutically equivalent dose of one or more other capsaicinoids, is administered via injection or implantation to produce a selective, highly-localized destruction or incapacitation of C-fiber and/or A-delta-fiber in discrete localized areas responsible for the initiation of pain for the purpose of eliminating pain arising from that locus, while minimizing potential adverse consequences of C-fiber and/or A-delta-fiber activation and/or damage outside of the locus of pain. In certain preferred embodiments, from about 10 to about 3000 micrograms of capsaicin, or a therapeutically equivalent dose of one or more other capsaicinoids, is administered at the site. In certain preferred embodiments, the amount of capsaicin and/or preferably the range of capsaicin administered at the site is from about 100 to about 1000 micrograms. In other words, the present invention is directed to administration of a single dose of capsaicin or other capsaicinoid(s) in an amount that is greatly reduced as compared to the dosage range previously considered useful by those skilled in the art to denervate the nerve fibers in a discrete, localized area without eliciting a systemic effect (e.g., an effect beyond that discrete, localized location).

Capsaicinoids (capsaicin analogues) with similar physiological properties, i.e., triggering C fiber membrane depolarization by opening of cation channels permeable to calcium and sodium, are known. For example, resiniferatoxin is described as a capsaicin analogue in U.S. Pat. No. 5,290,816 to Blumberg. U.S. Pat. No. 4,812,446 to Brand (Procter & Gamble Co.) describes other capsaicin analogues and methods for their preparation. U.S. Pat. No. 4,424,205 cites capsaicin analogues. Ton et al., Brit. J. Pharm. 10:175-182 (1955) discusses the pharmacological actions of capsaicin and its analogues. Capsaicin, capsaicin analogues and other capsaicinoids are also described in detail in WO 96/40079, the disclosure of which is hereby incorporated by reference. Capsaicinoids are also described in EPO 149 545, the disclosure of which is also hereby incorporated by reference.

Alternatively, capsaicioids (capsaicin analogues) may be administered at the site in replacement of, part of, or all of the dose of capsaicin, the capsaicin analogue being administered in a therapeutically equivalent amount of capsaicin for which it is substituted. Where a capsaicin analogue is selected to replace some or all of the capsaicin, the capsaicin analogue can be selected from those compounds with similar physiological properties to capsaicin as are known in the art. Resiniferatoxin qualitatively resembles capsaicin in its activity, but differs quantitatively in potency (i.e. $10^3$-$10^4$ fold more potent) and in relative spectrum of actions. For resiniferatoxin it is recommended to administer $0.1 \times 10^{-3}$ to $5 \times 10^{-2}$ mg/kg, preferably $0.1 \times 10^{-3}$ to $5 \times 10^{-3}$ mg/kg, body weight of the subject for single application, or less upon multiple application. In certain embodiments, resiniferatoxin is administered in the range of $1 \times 10^5$ mg/kg to $5 \times 10^{-2}$ mg/kg to the subject. Resiniferatoxin also shows a somewhat different spectrum of action, providing greater relief of pain at a given dose. Therefore, the dose of resiniferatoxin should be at least 100 fold less than a dose of capsaicin alone.

Other suitable capsaicinoids for use in the present invention include, but are not limited to, N-vanillylnonanamides, N-vanillylsulfonamides, N-vanillylureas, N-vanillylcarbamates, N[(substituted phenyl)methyl]alkylamides, methylene substituted N[(substituted phenyl)methyl]alkanamides, N[(substituted phenyl)methyl]-cis-monosaturated alkenamides, N[(substituted phenyl)methyl]diunsaturated amides, 3-hydroxyacetanilide, hydroxyphenylacetamides, pseudocapsaicin, dihydrocapsaicin, nordihydrocapsaicin, homocapsaicin, homodihydrocapsaicin I, anandamide, piperine, zingerone, warburganal, polygodial, aframodial, cinnamodial, cinnamosmolide, cinnamolide, civainde, nonivamide, olvanil, N-oleyl-homovanillamidia, isovelleral, scalaradial, ancistrodial, β-acaridial, merulidial, scutigeral and any combinations or mixtures thereof.

In certain embodiments, the capsaicinoid utilized in the compositions and methods of the invention is capsaicin itself. In certain preferred embodiments, the capsaicin is in a purified form obtained from the chemical purification of Capsaicin USP. In certain preferred embodiments, the purified capsaicin used in the compositions and methods of the invention consists essentially of the trans isomer. The trans-isomer of capsaicin has its activity at the vanilloid receptor, and this embodiment, the methods and formulation of the present invention are especially useful for treating disorders or pain that can be alleviated through activation of the vanilloid receptors via the VR-1 mechanism. Whereas Capsaicin USP contains only about 55-60% trans-capsaicin, with the remainder comprising the precursors dihydrocapsaicin and nordihydrocapsaicin, in such embodiments the formulation preferably consists essentially of trans-capsaicin, e.g., preferably having a purity of greater than about 97%, preferably greater than about 98%, more preferably greater than about 99% trans-capsaicin.

The trans isomer is preferably prepared in accordance with the method for synthesizing the trans isomer of capsaicin from a four step process and purified as describe in U.S. Provisional Application No. 60/461,164 filed Apr. 8, 2003, the disclosure of which is hereby incorporated by reference in its entirety. In accordance with U.S. Provisional Application No. 60/461,164 said method for synthesizing the trans isomer of capsaicin comprises a) alkylating 3-methyl butyne with halovaleric acid and/or -haloalkanic acid to obtain 8-methyl- 6-nonynoic acid and/or alkynoic acid analogues thereof; b) reducing said 8-methyl-6-nonynoic acid to obtain trans-8-methyl-nonenoic acid; c) activating the 8-methyl-nonenoic acid to obtain an acid chloride; and d) acylating 4-hydroxy-3-methoxybenzylamine hydrochloride with the acid chloride to obtain trans-capsaicin.

In certain embodiments, step a) of the method for preparation of the capsaicin for use in the present invention comprises the steps of: i) mixing anhydrous tetrahydrofuran (THF) with hexamethylphosphoramide (HMPA) and cooling the mixture to about −78° C. to about −75° C.; ii) adding to the mixture of step i) 3-methyl butyne followed by a dropwise addition of a base at a temperature from about −78° C. to about −65° C. to obtain a second mixture; iii) warming the second mixture up to about −30° C. and stirring for about 30 minutes; and iv) adding dropwise a solution of a halovaleric acid in anhydrous tetrahydrofuran at a temperature of about −30° C. for about 10 to about 15 minutes, then gradually warming to room temperature and stirring overnight to obtain a reaction mixture.

In certain other embodiments, there is provided a method for obtaining a crude step a) intermediate product further comprising the steps of: i) adding 3M hydrochloric acid (HCl) to a reaction mixture and extracting the reaction mixture with ethyl acetate; and ii) washing the extracted reaction mixture with brine to yield a crude product.

In certain embodiments, step b) of the method for preparation of the capsaicin for use in the present invention comprises the steps of: i) dissolving said 8-methyl-6-nonynoic acid in a mixture of anhydrous tetrahydrofuran and tertiary-butyl alcohol (t-BuOH) to obtain a solution and cooling the solution to about −55° C. to about −40° C.; ii) condensing ammonia ($NH_3$) to the solution to a temperature of about −50° C. to about −40° C.; iii) adding sodium drips piece-wise and stirring from about 30 minutes to about 2 hours at a temperature from about −45° C. to about −30° C., and iv) adding ammonium chloride ($NH_4Cl$), warming to room temperature and allowing the $NH_3$ to evaporate overnight to obtain a reaction mixture. Step iii) of the step b) reaction may further comprise adding piece-wise lithium and stirring from about 30 minutes to about 2 hours at a temperature from about −65 C to about −45 C.

In certain other embodiments crude step b) intermediate product further comprises the steps of: i) adding water to a reaction mixture; ii) acidifying the reaction mixture with 6N HCl to a pH of about 2 to about 3; iii) extracting the reaction mixture with ethyl acetate, washing with brine and drying over anhydrous sodium sulfate ($Na_2SO_4$); and iv) filtering and removing solvents under vacuum to obtain a crude step b) intermediate product.

In certain embodiments, step c) of the method for preparation of the capsaicin for use in the present invention comprises the steps of: i) adding dropwise a thionyl halide to the 8-methyl-nonenoic acid at room temperature for about 15 minutes to about 30 minutes to form a solution; ii) heating the solution at about 50° C. to about 75 C for a period of about 1 hour; and iii) removing excess thionyl halide under vacuum at about 40 C to about 45 C to obtain a step c) intermediate product.

In certain embodiments, step d) of the method for preparation of the capsaicin for use in the present invention comprises the steps of: i) mixing 4-hydroxy-3-methoxy benzylamine hydrochloride and dimethylformamide (DMF); ii) adding portion-wise at room temperature to the mixture of step i) 5N sodium hydroxide (NaOH) and stirring for about 30 minutes; iii) adding acid halide in anhydrous ether dropwise at a temperature of about 0° C. to about 10° C. for about 20 minutes to about 1 hour; and, thereafter, iv) gradually warming the mixture to room temperature and stirring overnight. In certain embodiments step d) further comprises the steps of: i) adding water to the mixture and extracting the mixture with ethyl acetate to obtain an ethyl acetate extract; ii) washing said extract with 1N HCl and, thereafter, washing with sodium bicarbonate ($NaHCO_3$); iii) washing the solution with brine and drying over anhydrous sodium sulfate ($Na_2SO_4$); and iv) filtering and removing solvents under vacuum to obtain a crude product.

In certain preferred embodiments, the method of preparing the trans-capsaicin or capsaicin intermediate after one or more of the steps (e.g., a), b), c) and/or d)) further comprises purifying the crude product by column chromatography, flash chromatography, or the like, using silica gel and eluting with a mixture of ethyl acetate/hexane to obtain a crude trans-capsaicin product.

Preferably after the capsaicin is formed via the four-step process as described above, the trans-capsaicin product is subjected to purification process comprising the steps of: i) dissolving the crude trans-capsaicin product in a mixture of ether/hexane and heating the mixture to about 40° C. to about 45° C.; ii) cooling the mixture to room temperature while stirring for about 2 hours; and iii) filtering the mixture to provide a purified trans-capsaicin product.

Alternatively, or additionally to the purification process (es) as described above, the capsaicin is subjected to a further purification process also referred to as a "semi-prep purification" or "semi-preparative purification" of capsaicin. In the semi-prep purification, the capsaicin or previously purified capsaicin is purified via the use of a semi-preparative HPLC (high performance liquid chromatography), which preferably provides for a trans-capsaicin product having a purity of greater than about 97%, preferably greater than about 98%, more preferably greater than about 99% capsaicin.

In certain preferred embodiments, the active ingredient in the preparation comprises substantially pure trans-capsaicin (e.g. having no more than about 10% precursors or other capsaicin compounds such as cis-capsaicin). In more preferred embodiments, the preparation includes at least about 95% pure trans-capsaicin. In most preferred embodiments, the preparation includes at least about 99% pure trans-capsaicin. While the cis-isomer of capsaicin has activity via a number of mechanisms, VR-1 is not considered to comprise a major effect of this agent.

In view of the collective activity of the trans-isomer of capsaicin at the VR-1 receptor, it is contemplated that it is possible in certain embodiments of the present invention that the amount of trans-capsaicin included in the methods and formulations of the present invention will be reduced in comparison to a preparation which includes a less pure form of capsaicin (e.g., capsaicin USP).

In other embodiments of the present invention, the formulations and methods of the invention contemplate the use of a capsaicin agent consisting essentially of cis-capsaicin.

Capsaicin, in either crude extract form, Capsaicin USP, or as purified capsaicin, has been comprehensively studied in a variety of tests in vitro, and in several animal species in vivo. Much of the data published can be found in the open scientific literature and in the proprietary studies discussed below (See: Examples I-XI).

Administration of a single dose of capsaicinoid according to the methods of the present invention minimizes and/or prevents systemic delivery of the capsaicin for the purposes of: a) producing a selective, highly-localized destruction or incapacitation of C-fibers and/or A-delta fibers in a discrete, localized area responsible for the initiation of pain (e.g., trigger points, intra-articular spaces, bursa) for the purpose of reducing or eliminating pain arising from a discrete locus (i.e., producing antinociception), and b) minimizing potential adverse consequences of C-fiber and/or A-delta activation and or damage outside of the locus of pain (i.e., damage to homeostatic mechanisms, such as cardiac reflex [e.g., Bezold-Jarisch reflex] or micturation reflex [e.g., urge to void] or to nerve fibers in the central nervous system). The analgesic effect preferably provides pain relief for at least about 48 to about 120 hours, preferably from about 10 to about 21 days, more preferably from about 4 to about 5 weeks, even more preferably for at least about 6 to about 8 weeks, and most preferably for at least about 16 weeks or more.

Delivery systems can also be used to administer capsaicin/capsaicinoid and local anesthetics that produce modality-specific blockade, as reported by Schneider, et al., Anesthesiology, 74:270-281 (1991), or possess physical-chemical attributes that make them more useful for sustained release then for single injection blockade, as reported by Masters, et al., Soc. Neurosci. Abstr., 18:200 (1992), the teachings of which are incorporated herein. An example of a delivery system includes microspheres wherein the anesthetic is incorporated into a polymer matrix in a percent loading of 0.1% to 90% by weight, preferably 5% to 75% by weight. It is possible to tailor a system to deliver a specified loading and subsequent maintenance dose by manipulating the percent drug incorporated in the polymer and the shape of the matrix, in addition to the form of local anesthetic (free base versus salt) and the method of production. The amount of drug released per day increases proportionately with the percentage of drug incorporated into the matrix (for example, from 5 to 10 to 20%). Other forms of delivery systems include microcapsules, slabs, beads, and pellets, which in some cases can also be formulated into a paste or suspension.

The delivery systems are most preferably formed of a synthetic biodegradable polymer, although other materials may also be used to formulate the delivery systems, including proteins, polysaccharides, and non-biodegradable synthetic polymers. It is most preferable that the polymer degrade in vivo over a period of less than a year, with at least 50% of the polymer degrading within six months or less. Even more preferably, the polymer will degrade significantly within a month, with at least 50% of the polymer degrading into non-toxic residues which are removed by the body, and 100% of the capsaicinoid and anesthetic being released within a two week period. Polymers should also preferably degrade by hydrolysis by surface erosion, rather than by bulk erosion, so that release is not only sustained but also linear. Polymers which meet this criteria include some of the polyanhydrides, poly(hydroxy acids) such as co-polymers of lactic acid and glycolic acid wherein the weight ratio of lactic acid to glycolic acid is no more than 4:1 (i.e., 80% or less lactic acid to 20% or more glycolic acid by weight), and polyorthoesters containing a catalyst or degradation enhancing compound, for example, containing at least 1% by weight anhydride catalyst such as maleic anhydride. Other polymers include protein polymers such as gelatin and fibrin and polysaccharides such as hyaluronic acid. Polylactic acid is not useful since it takes at least one year to degrade in vivo. The polymers should be biocompatible. Biocompatibility is enhanced by recrystallization of either the monomers forming the polymer and/or the polymer using standard techniques.

Other local carrier or release systems can also be used, for example, the lecithin microdroplets or liposomes of Haynes, et al., Anesthesiology 63, 490-499 (1985), or the polymer-phospholipid microparticles of U.S. Pat. No. 5,188,837 (Domb).

Methods for manufacture of suitable delivery systems for administration of capsaicinoid alone or together with the local anesthetic are known to those skilled in the art. The formulations may also be designed to deliver both the anesthetic and the capsaicinoid, either simultaneously or sequentially.

The local anesthetic can preferably be administered by direct injection, implantation or infiltration to the site where the capsaicinoid is to be administered, for example, by administering the local anesthetic directly in the diseased or pain producing structure or the injured nerve or the nerve that provides inervation to the painful area, or to effect a regional block of the area including the site where the capsaicin is to be administered.

In another embodiment, the local anesthetic can preferably be administered by injection, implantation or infiltration of the anesthetic into the epidural space adjacent to the spine for pain originating below a patient's waist, or directly into a joint for pain originating above the patient's waist. The prior administration of a proximal neural block sufficiently desensitizes C fibers to the expected pungent side effects of the subsequent capsaicinoid administration.

In embodiments where the anesthetic is administered as microspheres, the microspheres may be injected, implanted or infiltrated through a trochar, or the pellets or slabs may be surgically placed adjacent to nerves, prior to surgery or following repair or washing of a wound. The microspheres can be administered alone when they include both the capsaicin and local anesthetic or in combination with a solution including capsaicin in an amount effective to prolong nerve blockade by the anesthetic released from the microspheres. The suspensions, pastes, beads, and microparticles will typically include a pharmaceutically acceptable liquid carrier for administration to a patient, for example, sterile saline, sterile water, phosphate buffered saline, or other common carriers.

The expected side effects of the dose of the capsaicinoid are believed to be from the intense nociceptor discharge occurring during the excitatory phase before nociceptor desensitization. However, the prior administration of an anesthetic, such as a nerve block, proximally or directly to the site of administration, eliminates or substantially reduces such side effects. If some "breakthrough pain" occurs despite the anesthetic, this pain may be treated by administering an analgesic such as a nonsteroidal anti-inflammatory agent or narcotic analgesic (i.e., the various alkaloids of opium, such as morphine, morphine salts, and morphine analogues such as normorphine). The administration of the capsaicinoid can be repeated if necessary.

The compositions and methods of the present invention can be used for treating various conditions associated with pain by providing pain relief at a specific site. Examples of conditions to be treated include, but are not limited to, nociceptive pain (pain transmitted across intact neuronal pathways), neuropathic pain (pain caused by damage to neural structures), pain from nerve injury (neuromas and neuromas in continuity), pain from neuralgia (pain originating from disease and/or inflammation of nerves), pain from myalgias (pain originating from disease and/or inflammation of muscle), pain associated with painful trigger points, pain from tumors in soft tissues, pain associated with neurotransmitter-dysregulation syndromes (disruptions in quantity/quality of neurotransmitter molecules associated with signal transmission in normal nerves) and pain associated with orthopedic disorders such as conditions of the foot, knee, hip, spine, shoulders, elbow, hand, head and neck.

The receptors involved in pain detection are aptly enough referred to as nociceptor-receptors for noxious stimuli. These nociceptors are free nerve endings that terminate just below the skin as to detect cutaneous pain. Nociceptors are also located in tendons and joints, for detection of somatic pain and in body organs to detect visceral pain. Pain receptors are very numerous in the skin, hence pain detection here is well defined and the source of pain can be easily localized. In tendons, joints, and body organs the pain receptors are fewer. The source of pain therefore is not readily localized. Apparently, the number of nociceptors also influences the duration of the pain felt. Cutaneous pain typically is of short duration, but may be reactivated upon new impacts, while somatic and visceral pain is of longer duration. It is important to note that almost all body tissue is equipped with nociceptors. As explained above, this is an important fact, as pain has primary warning functions, for example, impinging on the well-being of the patient and thereby causing the patient to seek medical assistance. Nociceptive pain includes, but is not limited to post-operative pain, cluster headaches, dental pain, surgical pain, pain resulting from severe burns, post-partum pain, angina, genitor-urinary tract pain, pain associated with sports injuries (tendonitis, bursitis, etc. . . . ) and pain associated with joint degeneration and cystitis.

Neuropathic pain generally involves abnormalities in the nerve itself, such as degeneration of the axon or sheath. For example, in certain neuropathies the cells of the myelin sheath and/or Schwann cells may be dysfunctional, degenerative and may die, while the axon remains unaffected. Alternatively, in certain neuropathies just the axon is disturbed, and in certain neuropathies the axons and cells of the myelin sheath and/or Schwann cells are involved. Neuropathies may also be distinguished by the process by which they occur and their location (e.g. arising in the spinal cord and extending outward or vice versa). Direct injury to the nerves as well as many systemic diseases can produce this condition including AIDS/HIV, Herpes Zoster, syphilis, diabetes, and various autoimmune diseases. Neuropathic pain is often described as burning, or shooting type of pain, or tingling or itching pain and may be unrelenting in its intensity and even more debilitating than the initial injury or the disease process that induced it.

Neuropathies treatable by the methods of the present invention include: syndromes of acute ascending motor paralysis with variable disturbance of sensory function; syndromes of subacute sensorimotor paralysis; syndromes of acquired forms of chronic sensorimotor polyneuropathy; syndromes of determined forms of genetic chronic polyneuropathy; syndromes of recurrent or relapsing polyneuropathy; and syndromes of mononeuropathy or multiple neuropathies (Adams and Victor, Principles of Neurology, 4th ed., McGraw-Hill Information Services Company, p. 1036, 1989). Syndromes of acute ascending motor paralysis are selected from the group consisting of acute idiopathic polyneuritis, Landry-Guillain-Barre Syndrome, acute immune-mediated polyneuritis, infectious mononucleosis polyneuritis, hepatitis polyneuritis; diptheric polyneuropathy; porphyric polyneuropathy; toxic polyneuropathy (e.g., thallium); acute axonal polyneuropathy; acute panautonomic neuropathy; vaccinogenic, serogenic, paraneoplastic, polyarteretic and lupus polyneuropathy.

Syndromes of subacute sensorimotor paralysis are selected from the group consisting of deficiency states (e.g., beriberi, pellagra, vitamin B12); heavy metal/industrial solvent poisonings (e.g., arsenic, lead); drug overdose (e.g., isoniazid, disulfuram, vincristine, taxol, chloramphenicol); uremic polyneuropathy; diabetes; sarcoidosis; ischemic neuropathy and peripheral vascular disease; AIDS; and radiation (radiotherapy). Syndromes of chronic sensorimotor are selected from the group consisting of carcinoma, myeloma and other malignancies; paraproteinemias; uremia; beriberi (usually subacute), diabetes, hypo/hyperthyroidism; connective tissue disease; amyloidosis; leprosy and sepsis. Genetic chronic polyneuropathies are selected from the group consisting of dominant mutilating sensory neuropathy (adult); recessive mutilating sensory neuropathy (childhood); congenital insensitivity to pain; spinocerebellar degenerations, Riley Day Syndrome; Universal Anesthesia Syndrome; polyneuropathies w/ metabolic disorder; and mixed sensorimotor-autonomic type polyneuropathies. Recurrent/relapsing polyneuropathy are selected from the group consisting of idiopathic polyneuritis; porphyria; chronic inflammatory polyradiculoneuropathy; mononeuritis multiplex; beriberi/drug overdose; refsum disease and tangier disease. Mono/multiple neuropathies are selected from the group consisting of pressure palsies; traumatic neuropathies (e.g., irradiationor electrical injury); serum, vaccinogenic (e.g., rabies, smallpox); herpes zoster; neoplastic infiltration; leprosy; diptheretic wound infections; migrant sensory neuropathy; shingles and post herpetic neuralgia.

Neurotransmitter-dysregulation pain syndromes, rather than involving abnormal or damaged nerves, result from normal nerves having disruptions in the quantity and/or quality of the various neurotransmitter molecules associated with signal transmission from one neuron to another. More specifically, sensory transmitters are released from the afferent nerve ending of one nerve cell and received by receptors at the afferent end of another nerve cell. They are chemical messengers which transmit the signal. There are numerous transmitters, including glutamate, serotonin, dopamine, norepinephrine, somatostatin, substance P, calcitonin gene-related peptide, cholecystokinin, opiates and saponins. Alterations in the quantity of transmitters and neuropeptide release, changes in the afferent receptor, changes of re-uptake of the transmitter and/or neuropeptides can all yield qualitative change of the neural signaling process. As a result, the aberrant signal transmission is interpreted by the body as pain. A representative neurotransmitter dysregulation syndrome that may be treated by the present invention includes fibromyalgia, which is a common condition characterized by a history of chronic generalized pain and physical exam evidence of at least 11 of 18 defined "tender point" sites in muscles and connective tissue (Wolfe et al., Arthritis Rheum 33:160-72, 1990). Commonly associated conditions include irritable bowel syndrome, headache, irritable bladder syndrome (interstitial cystitis), sleep disturbance, and fatigue (Goldenberg, Current Opinion in Rheumatology 8:113-123, 1996; Moldofsky et al., Psychosom Med 37:341-51, 1975; Wolfe et al., 1990; Wolfe et al., J Rheum 23:3, 1996; Yunus et al., Semin Arthritis Rheum 11:151-71, 1981).

A predominant theory regarding the etiology of fibromyalgia holds that an imbalance and/or dysregulation of neurotransmitter function may occur within the central nervous system (CNS), either in the brain or spinal cord and in the relation of the CNS to muscle and connective tissue via regulatory nerve pathways (Goldenberg, 1996; Russell, Rheum Dis Clin NA 15:149-167, 1989; Russell et al., J Rheumatol 19:104-9, 1992; Vaeroy et al., Pain 32:21-6, 1988; Wolfe et al., 1996). Neurotransmitters are chemical messengers, amino acids, biogenic amines and neuropeptides, emitted from nerve cells that interact with receptors on other nerve cells, as well as other cell types, including muscle and immune cells. Neurotransmitter imbalance, which leads to increased pain experience, may include a qualitative and/or quantitative decrease in the function of such neurotransmitters as glutamate, serotonin, dopamine, norepinephrine, somatostatin, substance P, calcitonin gene-related peptide, cholecystokinin, opiates and saponins. Fibromyalgia is characterized by a relative deficit of serotonin effect and relative excess of substance P effect. This imbalance results in amplified modulation of pain-signaling in the central nervous system, resulting in neurogenic pain (Matucci-Cerinic, Rheumatic Disease Clinics of North America 19:975-991, 1993; Bonica, The Management of pain, Lea and Febiger, 2d ed., Philadelphia, pp. 95-121, 1990). Similar mechanisms may be at work to cause associated conditions; for example, dysregulation of neurotransmitter signaling in the bowel musculature, leading to irritable bowel syndrome symptoms such as cramping, diarrhea, and/or constipation.

Neurotransmitter-dysregulation pain syndromes include, but are not limited to the following: generalized syndromes, localized syndromes; craniofascial pain; vascular disease; rectal, perineum and external genitalia pain; and local syndromes of the leg/foot.

Generalized syndromes are selected from the group consisting of stump pain, causalgia, reflex sympathetic dystrophy, fibromyalgia or diffuse myofascial pain and burns. Localized syndromes are selected from the group consisting of trigeminal neuralgia; acute herpes zoster; panautonomic neuralgia; geniculate neuralgia (Romsay Hunt Syndrome); glossopharyngeal neuralgia; vagus nerve neuralgia and occipital neuralgia. Craniofacial pain includes temporomandibular pain. Suboccipital and cervical muskuloskeletal disorders are selected from the group consisting of myofascial syndrome, which includes cervical sprain cervical hyperextension (whiplash); sternocleidomastoid muscle; trapezius muscle; and stylohyoid process syndrome (Eagle's syndrome). Vascular disease is selected from the group consisting of Raynaud's disease; Raynaud's phenomenon; frosbite; erythema pernio (chilblains); acrocyanosis and livedo reticularis. Rectal, perineum and external genitalia pain are selected from the group consisting of iliohypogastric neuralgia; iliolinguinal nerve; genotifemoral nerve and testicular pain. Local syndromes of the leg/foot are selected from the group consisting of lateral cutaneous neuropathy (neuralgia paresthetica); oobturator neuralgia; femoral neuralgia; sciatica neuralgia; interdigital neuralgia of the foot (Morton's metatarsalgia or neurma); injection neuropathy and painful legs and moving toes.

Pain Intensity assessment scales are typically used by those of ordinary skill in the art to evaluate analgesic choices and therapeutic effects.

A Visual Analogue Scale (VAS) is a measurement instrument that measures a characteristic that is believed to range across a continuum of values and cannot easily be directly measured. For example, the amount of pain that a patient feels ranges across a continuum from none to an extreme amount of pain may be indirectly measured via the use of a VAS. Operationally a VAS is usually a horizontal line, 100 mm in length, anchored by word descriptors at each end, for example "no pain" at one end and "very severe pain" at the other end. The patient, marks on the line the point that they feel represents their perception of their current state. The VAS score is determined by measuring in millimeters from the left hand end of the line to the point that the patient marks. The 100-mm visual analog scale (VAS), a unidimensional scale that is versatile and easy to use, has been adopted in many settings.

The capsaicinoid formulations and methods described herein may be used to treat many conditions where the capsaicinoid can be administered via injection or implantation through the skin of the patient, including but not limited to the treatment of acute or chronic pain, nociceptive and neuropathic pain, pre- and post-operative pain, cancer pain, pain associated with neurotransmitter dysregulation syndromes and orthopedic disorders, sports-related injuries, acute traumatic pain, nociceptive pain, and neurotransmitter-dysregulation syndromes.

Treatment of Chronic Post-Herniorrhaphy Pain

In a preferred embodiment, the capsaicinoid formulations and methods disclosed herein can be used for the treatment/attenuation of chronic post-herniorrhaphy pain. Chronic post-herniorrhaphy pain occurs in between 5-30% of patients, with social consequences limiting some type of activity in about 10% of patients and 1-4% of patients are referred to chronic pain clinics. Nerve damage is probably the most plausible pathogenic factor, but specific principles for therapy have not been evidence-based and range from usual analgesics to re-operation with mesh removal and various types of nerve sections without any demonstrated efficacy in sufficient follow-up studies with or without randomized data. In patients suffering from pain associated with chronic post-herniorrhapy, the dose of capsaicinoid can be administered to the site where the surgery was performed or to the immediate area surrounding the incision.

Treatment of Pain Associated with Morton's Neuroma

In another preferred embodiment, the capsaicinoid formulations and methods disclosed herein can be used for the treatment/attenuation of pain associated with Morton's Neuroma. Morton's Neuroma is considered to be most likely a mechanically induced degenerative neuropathy which has a strong predilection for the third common digital nerve in middle-aged women. It is considered a well-defined model of neuropathic pain. The usual medical treatment of Morton's neuroma includes local injection of steroids, often with lidocaine. When nonsurgical means fail to relieve patient's symptoms, surgical removal of this offending neuroma through a dorsal approach can produce dramatic relief of symptoms in approximately 80% of patients. However, 20% of patients experience neuroma recurrence (referred to as stump or amputation neuroma) that often causes more severe pain that the original neuroma and is generally treatment resistant. Administration of capsaicinoid in accordance with the invention is useful for the treatment of the neuropathic pain associated with Morton's Neuroma and may reduce the re-occurrence of pain associated with stump or amputation neuroma.

Orthopedic Disorders

The capsaicinoid formulations and methods disclosed herein may be utilized to treat/attenuate pain associated with orthopedic disorders. Orthopedic disorders treatable via the use of the formulations and methods of the invention include but are not limited to disorders of the knee, shoulders, back, hip, spine, elbows, foot, hand and other disorders, which involve pain at a specific site or body space. Orthopedic disorders affecting these locations include, but are not limited to bursitis, tendonitis, osteoarthritis, and rheumatoid arthritis. Bursitis is the inflammation of a bursa. Bursae are saclike cavities or potential cavities that contain synovial fluid located at tissue sites where friction occurs (e.g., where tendons or muscles pass over bony prominences). Bursae facilitate normal movement, minimize friction between moving parts, and may communicate with joints. In the normal state, the bursa provides a slippery surface that has almost no friction. A problem arises when a bursa becomes inflamed. The bursa loses its gliding capabilities, and becomes more and more irritated when it is moved. When the condition called bursitis occurs, the slippery bursa sac becomes swollen and inflamed. The added bulk of the swollen bursa causes more friction within already confined spaces. Also, the smooth gliding bursa becomes gritty and rough. Movement of an inflamed bursa are painful and irritating. Bursitis usually occurs in the shoulder (subacromial or subdeltoid bursitis). Other sites include the olecranon (miners' elbow), prepatellar (housemaid's knee) or suprapatellar, retrocalcaneal (Achilles), iliopectineal (iliopsoas) of the hip, ischial (tailor's or weaver's bottom) of the pelvis, greater trochanteric of the femur, and first metatarsal head (bunion). Bursitis may be caused by trauma, chronic overuse, inflammatory arthritis (eg, gout, rheumatoid arthritis), or acute or chronic infection (eg, pyogenic organisms, particularly *Staphylococcus aureus*; tuberculous organisms, which now rarely cause bursitis). Orthopedic disorders of the foot include, but are not limited to, heel spurs, corns, bunions, Morton's neuroma, hammertoes, ankle sprain, fractures of the ankle or metatarsals or sesamoid bone or toes, plantar fasciitis and injuries to the achilles tendon. Orthopedic disorders of the hand include, but are not limited to, arthritis, carpal tunnel syndrome, ganglion cysts, tendon problems such as lateral epicondylitis, medial epicondylitis, rotator cuff tendonitis, DeQuervian's tenosynovitis, and trigger finger/trigger thumb. Other orthopedic disorders include, but are not limited to, Paget's disease, scoliosis, soft-tissue injuries such as contusions, sprains and strains, long bone fractures and various other sports injuries some of which include patellar tendonitis and lumbar strain.

Treatment of non-infected acute bursitis has mainly consisted of temporary rest or immobilization and high-dose NSAIDs, sometimes narcotic analgesics, may be helpful. Voluntary movement should be increased as pain subsides. Pendulum exercises are particularly helpful for the shoulder joint. Aspiration and intrabursal injection of depot corticosteroids 0.5 to 1 ml (triamcinolone diacetate 25 or 40 mg/ml) mixed with at least 3 to 5 ml of local anesthetic after infiltration with 1% local anesthetic (e.g., lidocaine) is the treatment of choice when rest alone is inadequate. The depot corticosteroid dose and volume of mixture are gauged to the size of the bursa. Reaspiration and injection may be required with resistant inflammation. Systemic corticosteroids (prednisone 15 to 30 mg/day or equivalent for 3 days) are occasionally indicated in resistant acute cases after infection and gout have been excluded. Chronic bursitis is treated as acute bursitis, except that splinting and rest are less likely to be helpful. Surgery is rarely needed to treat bursitis and is usually done only in the chronic cases that have not improved with traditional therapy. The most common surgical treatment, if needed, is an Incision and Drainage (called an I and D) and is used only in cases of infected bursa. The surgeon first numbs the skin with an anesthetic and then opens the bursa with a scalpel. Finally, the surgeon drains the fluid present in the inflamed bursa. Sometimes it is necessary to excise the entire bursa surgically. This is indicated only if the bursal swelling causes problems.

The capsaicinoid may be administered via injection in a location and fashion similar to that currently utilized with respect to localized injections of corticosteroids. For example, in certain embodiments, the dose of capsaicinoid is administered by intra-articular injection into the bursa.

Tendonitis

The capsaicinoid formulations and methods disclosed herein may be utilized to treat/attenuate pain associated with tendonitis (inflammation of the tendons). When tendons become inflamed, the action of pulling the muscle becomes irritating and painful. The cause is often unknown. Most instances tendonitis occurs in middle-aged or older persons as the vascularity of tendons attenuates; repetitive microtrauma may increase injury. Repeated or extreme trauma (short of rupture), strain, or excessive (unaccustomed) exercise is most frequently implicated. The most common cause of tendonitis is overuse. Commonly, individuals begin an exercise program, or increase their level of exercise, and begin to experience symptoms of tendonitis. The tendon is unaccustomed to the new level of demand, and this overuse will cause an inflammation and tendonitis. Tendonitis produces pain, tenderness and stiffness near a joint which is aggravated by movement.

General practitioners commonly use non-steroidal anti-inflammatory drugs (NSAIDs) to treat tennis elbow, but there are no trials to date that have compared them with other painkillers and one study found no clinically important benefit over placebo. Symptomatic relief is provided by rest or immobilization (splint or cast) of the tendon, application of heat for chronic inflammation or cold for acute inflammation (whichever benefits the patient should be used), local analgesic drugs, and NSAIDs for 7 to 10 days. A critical review of the role of various anti-inflammatory medications in tendon disorders found limited evidence of short-term pain relief and no evidence of their effectiveness in providing even medium term clinical resolution. Use of corticosteroid injections provides mixed results in relief of pain and at times insufficient evidence to support their use. Injection of the tendon sheath with a depot corticosteroid (eg, dexamethasone acetate, methylprednisolone acetate, hydrocortisone acetate) 0.5 to 1 mL mixed with an equal or double volume of 1% local anesthetic (eg, lidocaine) has been utilized as a treatment, depending on severity and site. The injection is made blindly or proximal to the site of maximum tenderness if the specific inflammation site cannot be identified. Particular care should be taken not to inject the tendon per se (which offers greater resistance) because it may be weakened and rupture in active persons. Reexamination of a less inflamed site 3 or 4 days later often discloses the specific lesion, and a second injection can be made with greater precision. Rest of the injected part is advisable to diminish risk of tendon rupture. Although complications associated with intrarticular and soft tissue steroid injection are relatively uncommon, when a complication does occur, it can result in severe and disabling consequences for the subject. A small proportion of subjects fail to respond to only one injection of corticosteroid and some subjects who initially improve at four weeks had worst symptoms by six months. Therefore with this lack of consensus, no good evidence to support the use of local corticosteroid injections and the unknown long-term side-effects of using steroids, an alternative treatment must be sought.

In one embodiment of the present invention, pain associated with tendonitis of the knee, shoulders, hip, pelvis, spine, elbows, leg and foot is treated with a capsaicinoid injection undertaken in similar fashion as a localized corticosteroid injection. For example, in embodiments where the capsaicinoid formulation is used for the treatment/attenuation of pain associated with tendonitis or bursitis of the shoulder, the dose of capsaicinoid can be administered by injection into the subacromial bursa with the needle inserted into the space between the acromium and the humerus on the lateral aspect of the shoulder.

Osteoarthritis

The capsaicinoid formulations and methods disclosed herein may be used to treat/attenuate pain associated with osteoarthritis (degenerative joint disease). Osteoarthritis is characterized by the breakdown of the joint's cartilage. Cartilage is the part of the joint that cushions the ends of bones. Cartilage breakdown causes bones to rub against each other, causing pain and loss of movement. Most commonly affecting middle-aged and older people, osteoarthritis can range from very mild to very severe. It affects hands and weight-bearing joints such as knees, hips, feet and the back. There are many factors that can cause osteoarthritis, including but not limited to age, genetics, obesity, sports-related activities, work-related activities, or accidents. Treatment of osteoarthritis focuses on decreasing pain and improving joint movement, and may include: Exercises to keep joints flexible and improve muscle strength; Many different medications are used to control pain, including corticosteroids and NSAIDs, glucocorticoids injected into joints that are inflamed and not responsive to NSAIDS. For mild pain without inflammation, acetaminophen may be used; heat/cold therapy for temporary pain relief; joint protection to prevent strain or stress on painful joints; surgery (sometimes) to relieve chronic pain in damaged joints; and weight control to prevent extra stress on weight-bearing joints.

Pain associated with osteoarthritis may be treated/attenuated with the capsaicinoid formulations administered, e.g., by intra-articular injection at the affected site, including but not limited to orthopedic disorders of the knee such as osteoarthritis, shin splints, medial tibial stress syndrome, bursitis, tendonitis (patellar tendinitis); tears of the anterior cruciate ligament (blown out knee), posterior cruciate ligament, medial collateral ligament and lateral collateral ligament; arthritis of the knee; meniscal cartilage tear; Runner's conditions such as iliotibial band syndrome and Pes Anserine bursitis; torn meniscus and limited cartilage defects of the knee; orthopedic disorders of the shoulders including, but not limited to, bursitis, dislocation, separation, impingement and tear of the rotator cuff, tendonitis, adhesive capsulitis (frozen shoulder) and fractures.

Rheumatoid Arthritis

The capsaicinoid formulations and methods disclosed herein may be used to treat/attenuate pain associated with rheumatoid arthritis. Rheumatoid arthritis is a chronic, systemic, inflammatory disease that chiefly affects the synovial membranes of multiple joints in the body. Because the disease is systemic, there are many extra-articular features of the disease as well. Rheumatoid Arthritis can affect many joints in the body, including the knee, ankle, elbow, and wrist. Joints that are actively involved with the disease are usually tender, swollen, and likely demonstrate reduced motion. The disease is considered an autoimmune disease that is acquired and in which genetic factors appear to play a role. The capsaicinoid may be administered via intra-articular injection in a location and fashion similar to that currently utilized with respect to localized injections of corticosteroids.

There are several different classes of drugs utilized to treat patients with the various types of rheumatic disease which maybe used in addition to the capsaicinoid treatment described herein, including analgesics to control pain, corticosteroids, uric acid-lowering drugs, immunosuppressive drugs, nonsteroidal anti-inflammatory drugs, and disease-modifying antirheumatic drugs.

Back Pain

The capsaicinoid formulations and methods disclosed herein may be used to treat/attenuate pain associated with back pain. Back pain is the second most common reason for doctor visits in the U.S. The causes of lower back pain are numerous. Some of the more common causes of lower back pain are: sudden injury to the back such as may occur in an auto accident, fall, sports, or other manner; gynecological conditions such as endometriosis, menstrual cramps, fibroid tumors, and pregnancy are sometimes the cause of lower back pain in women; and stress to the muscles, nerves, or ligaments in the lower back. Slipped discs, pinched nerves, sciatica, aging, and infections are other common causes of lower back pain. The treatment of lumbar strain consists of resting the back (to avoid re-injury), medications to relieve pain and muscle spasm, local heat applications, massage, and eventual (after the acute episode resolves) reconditioning exercises to strengthen the low back and abdominal muscles Zygapophysial joints, better known as facet or "Z" joints, are located on the back (posterior) of the spine on each side of the vertebrae where it overlaps the neighboring vertebrae. The facet joints provide stability and give the spine the ability to bend and twist. They are made up of the two surfaces of the adjacent vertebrae, which are separated by a thin layer of cartilage. The joint is surrounded by a sac-like capsule and is filled with synovial fluid (a lubricating liquid that reduces the friction between the two bone surfaces when the spine moves and also nourishes the cartilage.) A problem (such as inflammation, irritation, swelling or arthritis) in the facet joint may cause low back pain. Diagnostic tests can show an abnormality in a facet joint, which may suggest that the facet joint is the source of the pain. However, sometimes normal study results can be present while the facet joint is still the source of pain, and abnormal results do not always implicate the facet joint.

To determine if a facet joint is truly the source of back pain, an injection of local anesthetic (e.g, as a block) may be utilized. If an injection of a small amount of anesthetic or numbing medication into the facet joint reduces or removes the pain, it indicates that the facet joint may be the source of the pain. This is diagnostic use of the facet joint injection. Once a facet joint is pinpointed as a source of pain, therapeutic injections of anesthetic agents and anti-inflammatory medications may give pain relief for longer periods of time. The capsaicinoid formulations may be administered in such situations to attenuate such pain.

Facet joint injections are performed while the patient is awake, under a local anesthetic, and able to communicate. Sometimes, the health care provider may also administer drugs to make the patient more comfortable during the procedure. The injection is usually performed while the patient is lying on his or her stomach on an X-ray table. EKG, blood pressure cuffs and blood-oxygen monitoring devices may be hooked up prior to the injection process. Once the proper site has been determined, the physician will inject the anesthetic (often lidocaine or bupivicaine) and the anti-inflammatory (usually a corticosteroid.). This process may then be repeated depending on the number of affected facet joints.

The capsaicinoid may be administered via injection to treat back pain, e.g., in a location and fashion similar to that currently utilized with respect to localized injections of corticosteroids.

Heel Spur

The capsaicinoid formulations and methods disclosed herein may be used to treat/attenuate pain associated with a heel spur, which is a projection or growth of bone where certain muscles and soft tissue structures of the foot attach to the bottom of the heel. Most commonly, the plantar fascia, a broad, ligament-like structure extending from the heel bone to the base of the toes becomes inflamed, and symptoms of heel pain begin. As this inflammation continues over a period of time, with or without treatment, a heel spur is likely to form. If heel pain is treated early, conservative therapy is often successful and surgery is usually avoided. Early signs of heel pain are usually due to plantar fasciitis, the inflammation of the plantar fascia. It is probably the most common cause of heel pain seen by the podiatrist. It is seen in all groups of people; runners, athletes, week-end warriors, people who have jobs requiring a fair amount of standing, walking, or lifting, and those who have recently gained weight. Initially, patients receive taping of the foot and when indicated, cortisone injections or a short course an anti-inflammatory medication, taken orally. Exercises, night splints, and physical therapy are used as adjunct methods to try to reduce the inflammation. If successful, a custom made in shoe orthotic is made to control the abnormal stress and strain on the plantar fascia resulting in remission of the majority of the symptoms.

When capsaicinoid is used for the treatment of plantar fascia, the dose of capsaicinoid is preferably administered by injection into the affected area. When surgery is required, the capsaicinoid is preferably administered by infiltration into the heel bone.

Laparoscopic Cholecystectomy

The capsaicinoid formulations and methods disclosed herein may be used to treat/attenuate pain associated with laparoscopic cholecystectomy. Laparoscopic cholecystectomies have virtually replaced open surgical cholecystectomy. However, patients undergoing laparoscopic cholecystectomies still have pain. Pain control following surgery typically includes use of opioids, especially within the first several days after surgery. The administration of capsaicinoid in a patient who has undergone a laparoscopic cholecystectomy may reduce the amount of opioid consumption and postoperative pain scores associated with the procedure. In patients suffering from pain associated with a laparoscopic cholecystectomy, the dose of capsaicinoid can be administered either by injection, infiltration or both injection and infiltration. When the dose of capsaicinoid is administered by injection, the capsaicinoid may be injected directly the site of incision or to the immediate area surrounding the surgical site.

The capsaicinoid formulations and methods disclosed herein may be used to treat/attenuate pain associated with other laparoscopic surgical procedures, as well.

Dose

In preferred embodiments of the present invention, the dose of capsaicinoid contained in a unit dose injection/implantation is from about 1 µg to about 5000 µg of capsaicin, preferably from about 10 µg to about 3000 µg capsaicin, more preferably from about 300 µg to about 1500 µg capsaicin, or a therapeutically equivalent amount of one or more capsaicinoids. In certain preferred embodiments, the dose of capsaicin is from about 400 µg to about 1200 µg, or a therapeutically equivalent amount of one or more capsaicinoids. Preferably, the capsaicinoid is administered in a pharmaceutically and physiologically acceptable vehicle for injection or implantation.

In certain other embodiments, suitable doses of capsaicin/capsaicinoid for injection or implantation for the treatment of nociceptive pain, neuropathic pain, pain from nerve injury, pain from myalgias, pain associated with painful trigger points, pain from tumors in soft tissues, pain associated with neurotransmitter-dysregulation syndromes and pain associated with orthopedic disorders range from about 1 µg to about 3000 µg of capsaicin (trans 8-methyl-N-vanillyl-6-noneamide), preferably from about 20 to about 300 micrograms, more preferably from about 35 to 200 micrograms, with 100 µg most preferred.

In certain preferred embodiments, an injection of local anesthetic can be administered in proximity to the site prior to administration of the capsaicinoid, e.g., as described above and in the appended examples. In other embodiments, phenol can be used instead of or in addition to the local anesthetic.

Injectable/Implantable Formulations

In embodiments where the capsaicinoid is administered by injection, the capsaicinoid is administered to a discrete site by penetrating the outer layer of the skin with an instrument known to those skilled in the art for administering injections, e.g., a needle and syringe.

The dose of capsaicinoid is preferably prepared for injection/implantation by being incorporated into a pharmaceutically and physiologically acceptable vehicle for administration through the skin of the patient (e.g., human or animal). For example, the capsaicinoid may be dissolved in oils, propyleneglycol or other solvents commonly used to prepare injectable or implantable solutions. Suitable pharmaceutically acceptable vehicles preferably include aqueous vehicles, nonaqueous vehicles, antimicrobial agents, isotonic agents, buffers, antioxidants, suspending and dispersing agents, emulsifying agents, sequestering or chelating agents and any combinations or mixtures thereof. Examples of aqueous vehicles preferably include Sodium Chloride Injection, Bacteriostatic Sodium Chloride Injection, Ringers Injection, Isotonic Dextrose Injection, Sterile Water Injection, Bacteriostatic Sterile Water Injection, Dextrose Lactated Ringers Injection and any combinations or mixtures thereof. Nonaqueous parenteral vehicles preferably include fixed oils of vegetable origin, cottonseed oil, corn oil, sesame oil, peanut oil and any combinations or mixtures thereof. Antimicrobial agents in bacteriostatic or fungistatic concentrations preferably include phenols, cresols, mercurials, benzyl alcohol, chlorobutanol, ethyl and propyl p-hydroxybenzoic acid esters, thimerosal, benzalkonium chloride benzethonium chloride and mixtures thereof. Isotonic agents preferably include sodium chloride, dextrose and any combinations or mixtures thereof. Buffers preferably include acetate, phosphate, citrate and any combinations or mixtures thereof. Antioxidants preferably include ascorbic acid, sodium bisulfate and any combinations or mixtures thereof. Suspending and dispersing agents preferably include sodium carboxymethylcelluose, hydroxypropyl methylcellulose, polyvinylpyrrolidone and any combinations or mixtures thereof. Emulsifying agents preferably include Polysorbate 80 (Tween 80). Sequestering or chelating agents of metal ions preferably include ethylenediaminetetraacetic acid. Additional pharmaceutically acceptable vehicles also preferably include ethyl alcohol, polyethylene glycol, glycerin and propylene glycol for water miscible vehicles and sodium hydroxide, hydrochloric acid, citric acid or lactic acid for pH adjustment and any combinations or mixtures thereof.

Depending on the pharmaceutically acceptable vehicle chosen, the dose of capsaicinoid can be administered as an aqueous solution or suspension for injection or implantation. Injections are separated into five distinct types, generally classified as (i) medicaments or solutions or emulsions suitable for injection; (ii) dry solids or liquid concentrates containing no buffers, diluents, or other added substances, and which upon the addition of suitable vehicles, yield solutions conforming in all aspects to the requirements for injections; (iii) preparations as described in (ii) except that they contain one or more buffers, diluents or other added substances; (iv) solids which are suspended in a suitable fluid medium and which are not to be injected intravenously or into the spinal canal; and (v) dry solids, which upon the addition of suitable vehicles, yield preparations conforming in all respects to the requirements of Sterile Suspensions (see: H. C. Ansel, Introduction to Pharmaceutical Dosage Forms, 4th Edit., 1985, pg. 238).

In certain other embodiments, a surfactant can preferably be combined with one or more of the pharmaceutically acceptable vehicles previously described herein so that the surfactant or buffering agent prevents the initial stinging or burning discomfort associated with capsaicinoid administration, as a wetting agent, emulsifier, solubilizer and/or antimicrobial.

Suitable surfactants include, but are not limited to, sodium stearyl fumarate, diethanolamine cetyl sulfate, polyethylene glycol, isostearate, polyethoxylated castor oil, benzalkonium chloride, nonoxyl 10, octoxynol 9, polyoxyethylene sorbitan fatty acids (polysorbate 20, 40, 60 and 80), sodium lauryl sulfate, sorbitan esters (sorbitan monolaurate, sorbitan monooleate, sorbitan monopalmitate, sorbitan monostearate, sorbitan sesquioleate, sorbitan trioleate, sorbitan tristearate, sorbitan laurate, sorbitan oleate, sorbitan palmitate, sorbitan stearate, sorbitan dioleate, sorbitan sesqui-isostearate, sorbitan sesquistearate, sorbitan tri-isostearate), lecithin pharmaceutical acceptable salts thereof and combinations thereof. When one or more surfactants are utilized in the formulations of the invention, they may be combined, e.g., with a pharmaceutically acceptable vehicle and may be present in the final formulation, e.g., in an amount ranging from about 0.1% to about 20%, more preferably from about 0.5% to about 10%.

Buffering agents may also be used to provide drug stability; to control the therapeutic activity of the drug substance (Ansel, Howard C., "Introduction to Pharmaceutical Dosage Forms," 4$^{th}$ Ed., 1985); and/or to prevent the initial stinging or burning discomfort associated with capsaicin administration. Suitable buffers include, but are not limited to sodium bicarbonate, sodium citrate, citric acid, sodium phosphate, pharmaceutically acceptable salts thereof and combinations thereof. When one or more buffers are utilized in the formulations of the invention, they may be combined, e.g., with a pharmaceutically acceptable vehicle and may be present in the final formulation, e.g., in an amount ranging from about 0.1% to about 20%, more preferably from about 0.5% to about 10%.

In certain preferred embodiments, the pharmaceutical vehicle utilized to deliver the injectable capsaicinoid comprises about 20% PEG 300, about 10 mM histidine and about 5% sucrose in water for injection.

In other preferred embodiments, delivery systems can be used to administer a unit dose of capsaicinoid. The dose of capsaicinoid can preferably be administered as injectable or implantable microparticles (microcapsules and microspheres). The microparticles are preferably in a size and distribution range suitable for implantation or injection. The diameter and shape of the microparticles can be manipulated to modify the release characteristics. For example, larger diameter microparticles will typically provide slower rates of release and reduced tissue penetration and smaller diameters of microparticles will produce the opposite effects, relative to microparticles of different mean diameter, but of the same composition. In addition, other particle shapes, such as cylindrical shapes, can also modify release rates by virtue of the increased ratio of surface area to mass inherent to such alternative geometrical shapes, relative to a spherical shape. The diameter of microparticles preferably range in size from about 5 microns to about 200 microns in diameter.

In a more preferred embodiment, the microparticles range in diameter from about 20 to about 120 microns. In another embodiment of the present invention, the dose of capsaicinoid can be administered in the form of implantable pellets, rods and slabs. Methods for manufacture of microparticles, pellets, rods and slabs are well known in the art and include solvent evaporation, phase separation and fluidized bed coating.

When the preferred methods of the present invention provide for administration of a single dose of capsaicinoid alone, the single dose of capsaicin is preferably administered at a discrete site in an amount effective to denervate the discrete site without eliciting an effect outside the discrete location. The single dose is preferably administered in a nerve directly at the site where pain relief is needed, directly into the pain producing structure, or into a nerve that provides inervation to the painful area via injection or implantation. Injectable or implantable administration preferably includes, but is not limited to subcutaneous (under the skin), intramuscular (muscle), itrathecal, epidural, intraperitoneal, caudal, intradermal or intracutaneous (into the skin), intercostals at a single nerve, intra-articular (joints) or body spaces, intrasynovial (joint fluid), intraspinal (spinal column), intra-arterial (arteries) administrations and administration into other connective tissue compartments. As used herein "intraspinal" means into or within the epidural space, the intrathecal space, the white or gray matter of the spinal cord affiliated structures such as the dorsal root and dorsal root ganglia.

Examples of intra-articular administration include knee, elbow, hip, sternoclavicular, tempromandibular, carpal, tarsal, wrist, ankle, intervertebral disk, ligamentum flavum and any other joints subject to arthritic conditions. Examples of body spaces include pleura, peritoneium, cranium, mediastinum, pericardium, and bursae or bursal. Examples of bursae include acromial, bicipitoradial, cubitoradial, deltoid, infrapatellar, ishchiadica, and other bursa known to those skilled in the art to be subject to pain.

When the single dose of capsaicin is administered via injection, the injection volume of capsaicin will depend on the localized site of administration. Suitable injection volumes to be delivered preferably range from about 0.1 to about 20 ml, more preferably from about 0.5 to about 10 ml and most preferably from about 1.0 to about 5 ml, depending on the site to be treated.

The administration of the anesthetic along with the subsequent administration of the capsaicinoid formulations and methods of the invention alleviate or attenuate pain at the site for a prolonged period of time. With respect to joint pain, in certain preferred embodiments a single unit dose capsaicinoid injection or implantation attenuates pain at the site for at least about one month, more preferably at least about 3 months, and typically in certain embodiments from about 3 to about 6 months. With respect to pain associated with arthritic conditions such as osteoarthritis, in certain preferred embodiments a single unit dose capsaicinoid injection or implantation attenuates pain at the site for at least about 3 months to at least about 4 months. With respect to post-surgical pain, in certain preferred embodiments a single unit dose capsaicinoid injection or implantation attenuates pain at the site for at least about one week, and in certain embodiments for at least about 1 month. Patients can be monitored for pain relief and increased movement, in the situation where treatment is in a joint. The treatment can be repeated as necessary to control the symptoms.

Breakthrough Pain

The term "breakthrough pain" means pain which the patient experiences despite the fact that the patient is being or was administered generally effective amounts of, e.g., capsaicin. In conjunction with the use of the capsaicinoid formulations and methods described herein, it is contemplated that it is nonetheless possible that the patient will experience breakthrough pain. For the treatment of breakthrough pain, the individual may be further administered an effective amount of an analgesic in accordance with the treatment of pain in such situations performed by those skilled in the art. The analgesic may be any known to the person skilled in the art such as those selected from the group comprising gold compounds such as sodium aurothiomalate; non-steroidal anti-inflammatory drugs (NSAIDs) such as naproxen, diclofenac, flurbiprofen, ibuprofen ketoprofen, ketorolac, pharmaceutically acceptable salts thereof and the like; opioid analgesics such as codeine, dextropropoxyphene, dihydrocodeine, morphine, diamorphine, hydromorphone, hydrocodone, methadone, pethidine, oxycodone, levorphanol, fentanyl and alfentanil, para-aminophenol derivatives such as paracetamol, pharmaceutically acceptable salts thereof and the like; and salicylates such as aspirin.

DETAILED DESCRIPTION OF THE PREFERRED EMBODIMENTS

Example I

Osteoarthritis of the Knee Safety Study

The following clinical study was carried out in order to evaluate the safety, tolerability, systemic pharmacokinetics, and efficacy of purified capsaicin administered by intra-articular infiltration together with a local anesthetic administered by intra-articular infiltration in subjects with osteoarthritis of the knee.

The primary objective of the study was to evaluate the safety and tolerability of intra-articular capsaicin, when co-administered with intra-articular local anesthetic, compared to placebo, in subjects with end-stage osteoarthritis of the knee, already scheduled to receive knee replacements.

Purified capsaicin was supplied in vials containing 5 mL of purified capsaicin at a concentrations of 500 µg/mL. Study drug was stored at a temperature between 15° C. and 25° C. Within four hours prior to injection, vehicle was used to dilute the drug to final concentrations of purified capsaicin, as follows:

TABLE 1

| Dose Level | Concentration | Total Volume of Dose |
|---|---|---|
| 10 µg | 2 µg/mL | 5 mL |
| 100 µg | 20 µg/mL | 5 mL |
| 300 µg | 60 µg/mL | 5 mL |

Each vial was used for one infiltration administration only and appropriately labeled. The supplier of the purified capsaicin was FormaTech, Inc., 200 Bullfinch Drive, Andover, Mass. 01810. The vials were supplied in bulk to the study center with each vial labeled according to the contents of the vial. The Pharmacist/Study Nurse, who prepared the injection, maintained the investigational product in a lockable cabinet at the required temperature, 15-25° C. The study blind was maintained by the Pharmacist/Study Nurse.

Placebo vehicle for purified capsaicin was supplied in vials containing 5 mL. Local anesthetic (Lignocaine 2%) was used for each intra-articular infiltration.

The study was a single center, randomized, double blind, placebo controlled, dose ranging Phase 1 study of three dose levels (10 µg, 100 µg, or 300 µg) of intra-articularly administered purified capsaicin, when co-administered with intra-articular local anesthetic, in subjects with osteoarthritis of the knee who were scheduled to undergo total knee replacement. The doses of purified capsaicin used in this trial were well below (>100 fold) doses known to be toxic to animals. The study was designed to include 16 evaluation subjects. Sixteen subjects were enrolled in the study; 12 were treated with ultra-purified capsaicin (4 each with 10, 100, and 300 µg doses) and 4 were treated with placebo vehicle. Sixteen subjects completed the study.

Patients were treated randomly and in double-blind fashion in four treatment cohorts, with each cohort having a progressively longer interval between the intra-articular administration of study medication and subsequent total knee replacement (2, 4, 7, and 14 days). Four subjects, 1 in each of the 4 dose groups (placebo, 10 µg, 100 µg, and 300 µg of capsaicin), were enrolled in each treatment cohort. Gross and microscopic pathology analysis was completed for each treatment cohort before the next treatment cohort was treated.

Each subject had 3 study visits: a Screening Day (Day −7 to −1), the Treatment Day (Day 0), and a Post-Treatment Day (scheduled for Day +2, +4, +7, or +14). On the Treatment Day the subject was randomized, pre-treatment evaluation was performed. The patients were brought into the procedure room, and a VAS pain score was taken (0 mm—no pain, 100 mm—extreme pain). Once the patient had marked his or her pain on the card, he/she was prepped for knee cannulation. Once the cannula was placed, the patient received by intra-articular infiltration, 3 mg/kg (maximum dose of 200 mg) of 2% lignocaine into the knee scheduled to be replaced. This administration of local anesthetic was followed in 10 minutes by an intra-articular infiltration of placebo (vehicle) or 10 µg, 100 µg, or 300 µg of purified capsaicin diluted with vehicle to a total volume of 5 mL.

VAS pain scores as well as verbal reports were taken immediately following administration, as well as prior to knee replacement surgery. No subjects discontinued from the study due to adverse events.

Immediately following instillation of capsaicin, some patients (0 of 4 receiving placebo, 0 of 4 receiving 10 µg capsaicin, 1 of 4 receiving 100 µg capsaicin, and 4 of 4 receiving 300 µg capsaicin) reported transient burning pain representative of capsaicin injection (onset within a few seconds to minutes and lasting less than one hour). Pain was mild but for some patients, the investigator chose to place ice packs on the treated knee until the pain resolved. In particular, the subject in the 100 µg dose group and 2 of the subjects in the 300 µg dose group had burning post-administration (hyper) algesic pain alone; two subjects in the 300 µg dose group had burning pain in conjunction with other types of post-administration (hyper) algesic pain (1 subject had burning and stinging pain and the second subject had burning and toothache-like pain). All of the episodes of post-administration (hyper) algesia began immediately (within 5 minutes) after administration. All of these painful episodes were brief: the duration of this pain was 9 minutes for the subject in the 100 µg dose group, and 17, 25, 25, and 42 minutes for the subjects in the 300 µg dose group. The 4 subjects in the 300 µg dose group and 1 subject in the 100 µg dose group required intervention for their post-injection (hyper) algesia. For all but 1 of these 5 subjects, the only intervention was ice packs. One subject in the 300 µg dose group was treated with paracetamol; no subjects were treated with intravenous morphine or granisetron for post-administration (hyper) algesia. Most of the concomitant medications used in the study were medications taken prior to the study that continued to be taken during the study. The only concomitant non-drug treatments during the study were the ice packs used in the 5 subjects with post-administration (hyper) algesia.

Figure 2:
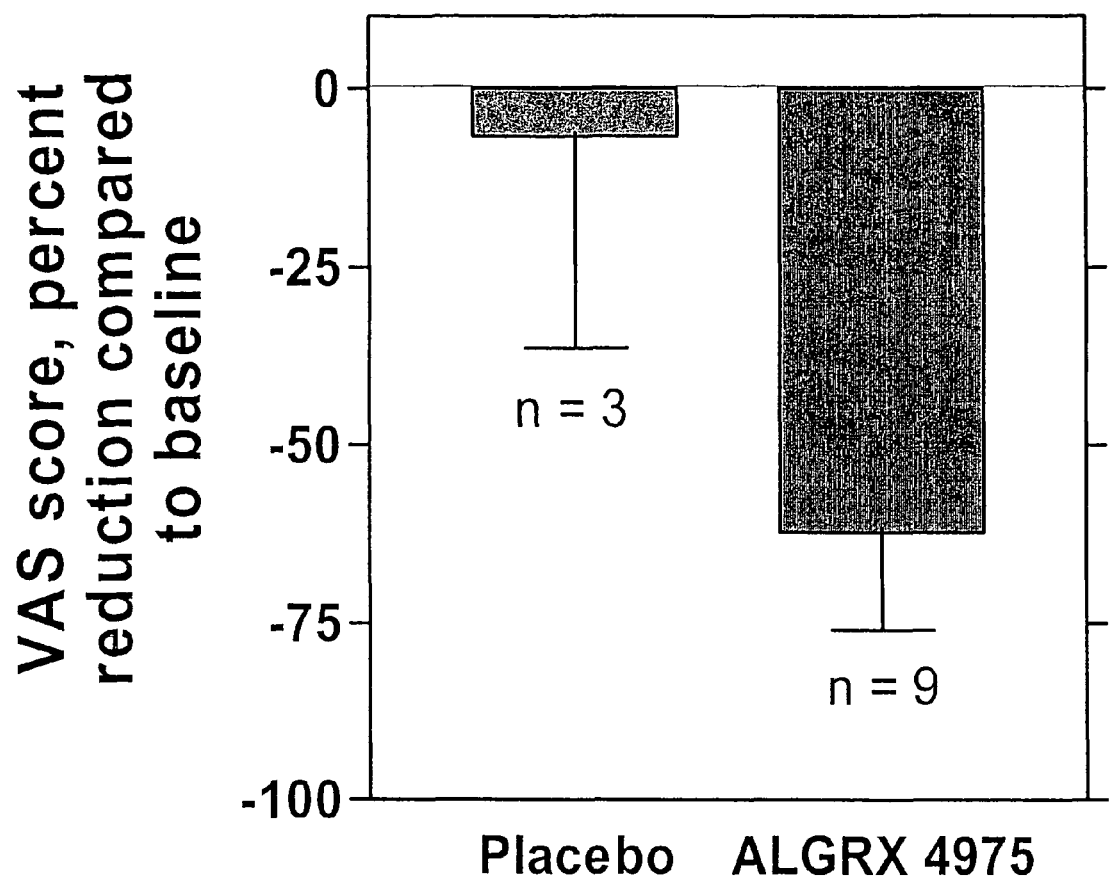
FIG. 2 is a graph displaying the percent reduction in VAS score compared to baseline in study subjects entered into the Osteoarthritis Safety Study exemplified in Example 1.

On the Post-Treatment Day, study evaluation was performed followed by the scheduled knee replacement, with intra-operative bone and soft tissue biopsies performed for subsequent examination. For overall efficacy analysis, we chose to exclude the patients who had surgery two days following administration since analgesia from remaining lignocaine or residual pain from the actual procedure (large volume infiltration) and lysing c-fiber endings could not be excluded (In normal volunteers, a mild "aching" pain is sometimes observed for up to two days following capsaicin administration). This therefore left the 3 placebo and 9 active patients from the 4 day, 7 day, and 14 day cohorts. Examination of the VAS scores prior to drug/placebo administration and the day of surgery (prior to surgery) showed that pain scores were not reduced in the placebo group (VAS decreased by only 7±30%), but was reduced in the capsaicin group (VAS reduced by 62±14%). The changes in VAS score are reported graphically as shown in FIG. 1. The plasma concentration over time of the three dosage ranges of capsaicin are shown in FIG. 2.

Ten-mL blood samples for subsequent assay of plasma ultra-purified capsaicin concentrations were collected prior to study medication administration, at 30 minutes, 1, 2, and 4 hours after study medication injection, and immediately prior to the first administration of pre-operative medications on the Post Treatment Day. The pharmacokinetic parameters of Cmax, Tmax, AUC(0–$t_{last}$) and t½ were evaluated.

In the 10 μg dose group, purified capsaicin plasma concentrations were measurable at only 0, 1, or 2 time points; therefore, no pharmacokinetic parameters could be estimated for any subject in this dose group. For the 3 subjects in each of the 100 μg, and 300 μg dose groups for which pharmacokinetic parameters could be estimated, the magnitude of the Cmax and AUC (0–$t_{last}$) values was similar in the 2 dose groups. Tmax values were 0.5 hr in all subjects for which they could be estimated. Terminal exponential half-lives were similarly brief in all subjects in both the 100 μg and 300 μg dose groups.

The AUC (0–$t_{last}$) values for the subjects in the 100 μg dose group (366.10, 75.19, and 511.21 pg*hr/mL) were similar in magnitude to the values for the 300 μg dose group (449.01, 220.42, and 498.83 pg*hr/mL). Similarly, the $C_{max}$ values in the 100 μg dose group (292.06, 79.94, and 538.32 pg/mL) were similar in magnitude to the values in the 300 μg dose group (207.62, 251.42, and 499.88 pg/mL). $T_{max}$ was 0.5 hours in all 6 subjects. The terminal exponential half lives were brief in all subjects, with values of 0.1498, 1.1488, and 0.1014 hr in the 100 μg dose group and values of 0.3268, 0.2298, and 0.1663 in the 300 μg dose group.

The pharmacokinetic conclusions are necessarily limited, because the number of timepoints at which plasma concentrations of purified capsaicin was measurable was so limited in these study subjects. However, there was some evidence for a pharmacokinetic dose response over the 10 μg to 300 μg dose range in that the purified capsaicin plasma concentrations in the 10 μg dose group were clearly lower than in either the 100 μg or the 300 μg dose groups. However, there was little evidence for a pharmacokinetic dose response over the 100-300 μg dose range.

Purified capsaicin was well tolerated at all dose levels. There was low leakage of study drug from the joint space and gross and microscopic pathology was normal. There were no treatment related signs of erythema, edema, or hemorrhage at the site of injection, and no treatment related effects on soft tissue, cartilage, or bone upon histopathological examination. No treatment related systemic side effects were seen, and there were no treatment related effects on laboratory safety parameters or vital signs. There was no discernable effect on proprioception at the injected knee in any dose group at any time point.

There was a clear dose response for the incidence of post injection hyperalgesia. This symptom occurred in 4 subjects in the 300 μg dose group, 1 subject in the 100 μg dose group, and no subjects in the 10 μg dose group or placebo. In all but one case, the hyperalgesia was described as a burning sensation, which developed within five minutes of injection and lasted on average less than thirty minutes. In all cases where intervention was required, the hyperalgesia was easily and effectively controlled by the application of ice packs to the knee.

Subjects were asked to rank their level of pain on a visual analogue scale (VAS), anchored by "no pain" on the left and "extreme pain" on the right, prior to receiving the intra-articular dose of purified capsaicin and local anesthetic and then again just prior to administration of preoperative medications on the day of knee replacement surgery. No clear treatment related indication of efficacy was seen at any of the dose levels (10 μg, 100 μg, and 300 μg) of purified capsaicin.

Since intra-articular infiltration of local anesthetic followed by intra-articular infiltration of capsaicin was generally well-tolerated, and the median decreases from baseline to the pre-operative time point in the VAS for pain at the target knee in all 3 capsaicin dose groups were all substantially greater that the median change from baseline in the placebo group, the risk to benefit ratio of this treatment strategy appears favorable. Further studies of this treatment in larger numbers of subjects with osteoarthritis appear warranted.

Example II

Osteoarthritis of the Knee Efficacy Study

The following clinical study evaluates the efficacy of purified capsaicin administered by intra-articular infiltration together with a local anesthetic injected by intra-articular infiltration in subjects with osteoarthritis of the knee.

The primary objective of the study is to evaluate the efficacy of intra-articular capsaicin, when co-administered with intra-articular local anesthetic, compared to placebo, in subjects with end-stage osteoarthritis of the knee, already scheduled to receive knee replacements (21 and 42 days after injection of study medication).

Purified capsaicin is supplied in vials containing 5 mL of purified capsaicin at a concentrations of 500 μg/mL. Study drug was stored at a temperature between 15° C. and 25° C. Within four hours prior to injection, vehicle is used to dilute the drug to final concentrations of purified capsaicin, as follows:

TABLE 2

| Dose Level | Concentration | Total Volume of Dose |
| --- | --- | --- |
| 1000 μg | 200 μg/mL | 5 mL |

Each vial is used for one infiltration administration only and appropriately labeled. The supplier of the purified capsaicin is FormaTech, Inc., 200 Bullfinch Drive, Andover, Mass. 01810. The vials are supplied in bulk to the study center with each vial labeled according to the contents of the vial. The Pharmacist/Study Nurse, who prepares the injection, maintains the investigational product in a lockable cabinet at the required temperature, 15-25° C. The study blind is maintained by the Pharmacist/Study Nurse.

Placebo vehicle for purified capsaicin is supplied in vials containing 5 mL. Local anesthetic (Lignocaine 2%) is used for each subacromial bursa infiltration.

The study is a single center, randomized, double blind, placebo controlled, dose ranging Phase 2 study of capsaicin (1000 μg) administered by intra-articular infiltration, when co-administered with intra-articular local anesthetic, in subjects with osteoarthritis of the knee who are scheduled to undergo total knee replacement from three to six weeks post study drug administration, wherein the primary endpoint is pain reduction at three weeks following study drug administration.

The study is designed to include 12 evaluation subjects (Patients suffering a defined pain:>40 mm on VAS). Six (6) subjects will be treated with capsaicin 1000 µg and 6 subjects will be treated with placebo vehicle. Patients are treated randomly and in double-blind fashion. Gross and microscopic pathology analysis are completed for each treatment group. Each subject has 3 study visits: a Screening Day (Day −7 to −1), the Treatment Day (Day 0), and a Post-Treatment Day (scheduled for Day +2, +4, +7, or +14). On the Treatment Day the subject is randomized, pre-treatment evaluation is performed. The patient is brought into the procedure room, and a VAS pain score is taken (0 mm—no pain, 100 mm—extreme pain). Once the patient marks his or her pain on the card, he/she is prepped for knee cannulation. Once the cannula is placed, the patient receives, by intra-articular infiltration, 3 mg/kg (maximum dose of 200 mg) of 2% lignocaine into the knee scheduled to be replaced. This infiltration of local anesthetic is followed in 10 minutes by an intra-articular infiltration of placebo (vehicle) or 1000 µg of purified capsaicin diluted with vehicle to a total volume of 5 mL.

VAS pain scores as well as verbal reports are taken immediately following administration, as well as prior to knee replacement surgery. On the Post-Treatment Day, a study evaluation is performed followed by the scheduled knee replacement, with intra-operative bone and soft tissue biopsies performed for subsequent examination. For overall efficacy analysis, patients having surgery two days following infiltration are excluded since analgesia from remaining lignocaine or residual pain from the actual procedure (large volume injection) and lysing c-fiber endings is not capable of being excluded.

Changes in NRS (Numerical Rating Scale) pain scores were measured at three weeks following administration. Final NRS score for placebo=7.30 (p=0.05), whereas final NRS score for capsaicin=3.97 (P=0.03) (See FIG. 3).

Example III

Bunionectomy Efficacy Study

The following study was carried out in order to evaluate the safety, tolerability, systemic pharmacokinetics, and efficacy of intra-operative (infiltration) capsaicin when co-administered with a local anesthetic in patients scheduled to undergo transpositional osteotomy (bunionectomy).

The primary objective of the study was to evaluate the safety and tolerability of capsaicin, when co-administered by intra-articular infiltration with a local anesthetic, compared to placebo, in subjects with hallux valgus deformity, already scheduled to undergo transpositional osteotomy (bunionectomy). The secondary objective of the study was to evaluate the safety, tolerability and systemic pharmacokinetics of purified capsaicin following intra-operative administration. The primary efficacy endpoint was the proportion of subjects in each treatment group requiring opioid analgesia in the first 24 hours post-operatively. The proportions were compared amongst treatment groups using the Cochran-Haenszel test. Secondary efficacy end points included: i) proportion of subjects in each treatment group requiring opioid analgesia in the first 36 hour period post-operatively (Similarly, the proportions were compared amongst treatment groups using the Cochran-Haenszel test); ii) proportion of subjects in each treatment group requiring opioid analgesia in the 10 day period post-operatively (Similarly, the proportions were compared amongst treatment groups using the Cochran-Haenszel test); iii) time to first usage of opioid analgesia in each treatment group (a survival analysis approach will be used: the product-limit (Kaplan-Meier) method will be applied to time to first usage of opioid analgesia. The median time to first usage of opioid analgesia will be estimated in both treatment groups. Pairwise comparisons will be performed to test for equality of the survival curves between the 2 treatment groups using both the log-rank and the Wilcoxon test); iv) total usage of analgesia in each treatment group (the total usage of analgesia will be compared by an analysis of variance with treatment and center as independent variables. A pairwise comparison will be performed between the treatment groups); and v) VAS assessment of pain at the site of operation in each treatment group (The VAS score at each time point will be compared by an analysis of variance with treatment and center as independent variables. A pairwise comparison will be performed between the treatment groups). Safety endpoints included: i) laboratory safety parameters; ii) adverse events; and iii) purified capsaicin blood levels. The efficacy analysis was performed on the data obtained ten days postoperatively. The safety analysis was performed based on the safety data for the entire study, including the 6 week and 12 week follow-up periods. The blind was broken at the time the efficacy analysis was performed. However, the individual treatment assignment was available to the statistical analysis group only. All other personnel involved in the study, including the Investigator, study monitor and proprietary staff, remained blinded until the entire study was completed.

Purified capsaicin was supplied in vials containing 5 mL of purified capsaicin at a concentrations of 500 µg/mL. Study drug was stored at a temperature between 15° C. and 25° C. Within four hours prior to injection, vehicle was used to dilute the drug to final concentrations of purified capsaicin, as follows:

TABLE 3

| Dose Level | Concentration | Total Volume of Dose |
| --- | --- | --- |
| 1000 µg | 250 µg/mL | 4 mL |

Each vial was used for one infiltration administration only and appropriately labeled. The supplier of the purified capsaicin was FormaTech, Inc., 200 Bullfinch Drive, Andover, Mass. 01810. The vials were supplied in bulk to the study center with each vial labeled according to the contents of the vial. The Pharmacist/Study Nurse, who prepared the injection, maintained the investigational product in a lockable cabinet at the required temperature, 15-25° C. The study blind was maintained by the Pharmacist/Study Nurse.

Placebo vehicle for purified capsaicin was supplied in vials containing 5 mL. Local anesthetic (Lignocaine 2%) was used for each infiltration.

The study was a single center, randomized, double blind, placebo controlled, Phase II study of the safety and efficacy of intra-operative capsaicin, when co-administered with local anaesthetic, in subjects undergoing transpositional first metatarsal osteotomy and fixation for the correction of hallux valgus deformity. The dose of capsaicin used in the trial was 1000 µg.

The study was designed to include 40 evaluation subjects. Twenty (20) randomized to the capsaicin treatment group and twenty (20) to the placebo control group. Each subject had six (6) study visits: a Screening Day (Day −28 to −1), an Operation Day (Day 0), and four (4) Follow-up visits (scheduled for Days 3, 10 and weeks 6 and 12).

On Operation Day (Day 0) the following was performed: a) Pre-operation: Prior to the initiation of an ankle block, inclusion/exclusion criteria assessment was performed. Eligible subjects were randomized, pre-treatment evaluation was performed, which included laboratory safety assessments, measurement of vital signs, VAS assessment of pain at the target Hallux valgus, blood sample measurement for purified capsaicin concentration, and review of concomitant medications; b) Operation: An ankle block [lidocaine 0.5% (up to a total of 20 ml)] was initiated by the investigator to provide surgical anesthesia, and then a transpositional osteotomy of the first metatarsal+/−an Akin osteotomy of the proximal phalanx in accordance with normal practices and procedures was performed. Immediately prior to wound closure, the Investigator slowly dripped the study medication (4 mL) from a syringe into the wound, ensuring even tissue exposure. The wound was then closed according to normal practices and procedures.

Post-Operation:

In the 24 hours following administration of study medication, vital signs (supine pulse rate and blood pressure) were recorded at 1, 2, 4 and 24 hours post administration. VAS assessment of pain at the operation site was performed at 1, 4, 8, 12 and 24 hours post administration. In those instances where VAS measurements coincide with blood sampling procedures, the VAS assessment was performed first. Blood samples for measurement of capsaicin concentration were obtained at 1, 2, and 4 hours post administration. The quantity of each blood sample was 10 mL. Laboratory safety assessments, e.g., haematology, biochemistry, urinalysis were performed at 24 hours post administration. Adverse events were spontaneously reported by the subject and recorded. Rescue analgesia medication was provided to the subject if required (initially diclofenac 50 mg, repeated at 8 hourly intervals if necessary). When diclofenac was judged by the Investigator to provide inadequate pain relief then the subject was provided with alfentanil, 1 mg, repeated at 6 hourly intervals when necessary. Upon discharge from the hospital, alfentanil was substituted with co-codamol 30/500 (codeine phosphate 30 mg+paracetamol 500 mg), repeated at 4 hourly intervals when necessary. Any usage of rescue medication or concomitant medication was recorded in the subject's CRF. At 24 hours post administration of study medication, the subject was discharged from the clinic.

Follow Up:

Follow-up (days 1-10): Upon discharge from the clinic, the subject was provided with a diary card for Days 1-10, and asked to record: VAS assessment of pain at the operation site, performed each morning; time and amount of any rescue medication taken by the subject (at any time); usage of concomitant medications (at any time); adverse events experienced by the subject (at any time). Each subject was also be asked to return to the clinic on Day 3 and on Day 10 post-operation. At these clinic visits the Investigator examined the subject's diary card and resolved any unclear or inconsistent entries. Data from the diary card was transcribed to the subject's CRF. The site of the operation was inspected by the Investigator to confirm that normal wound healing took place.

Follow Up (Week 6): The subject was asked to return to the clinic at 6 weeks post operation. The site of the operation was inspected by the Investigator to confirm that normal wound healing is took place. The subject was questioned about any adverse events he/she experienced since the last clinic visit, and any usage of concomitant medication.

Follow Up (Week 12): The subject was asked to return to the clinic at 12 weeks post operation. The site of the operation was inspected by the Investigator to confirm that normal wound healing is took place. The subject was questioned about any adverse events he/she may experienced since the last clinic visit, and any usage of concomitant medication. The Investigator discharge the subject from the study.

Figure 3:
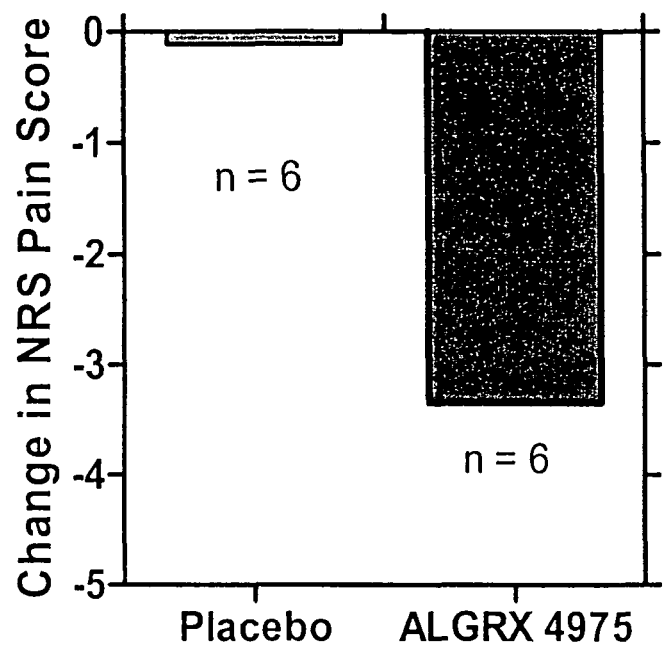
FIG. 3 is a graph displaying the NRS Pain Score in study subjects entered into the Osteoarthritis Efficacy Study exemplified in Example 2.
Figure 4:
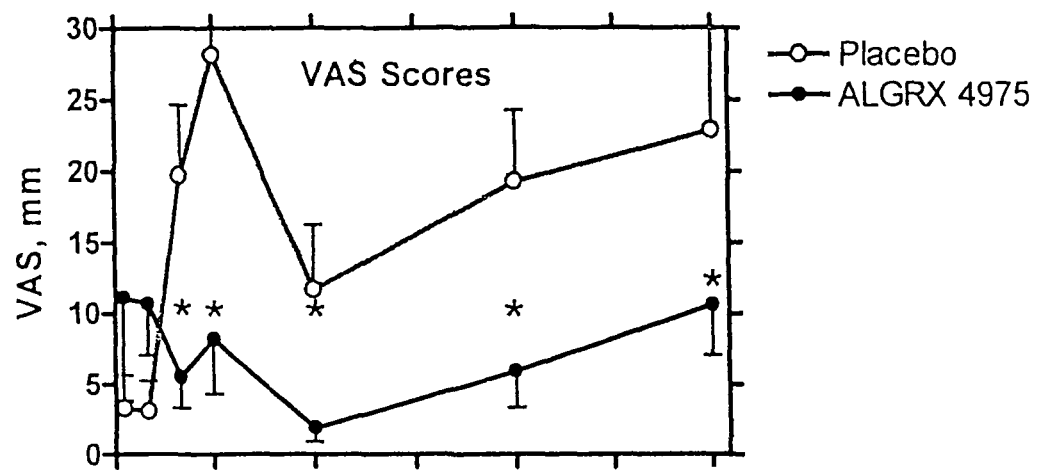
FIG. 4 is a graph displaying a comparison of VAS Pain Score between subjects entered into the Bunionectomy Efficacy study exemplified in Example 3.
Figure 5:
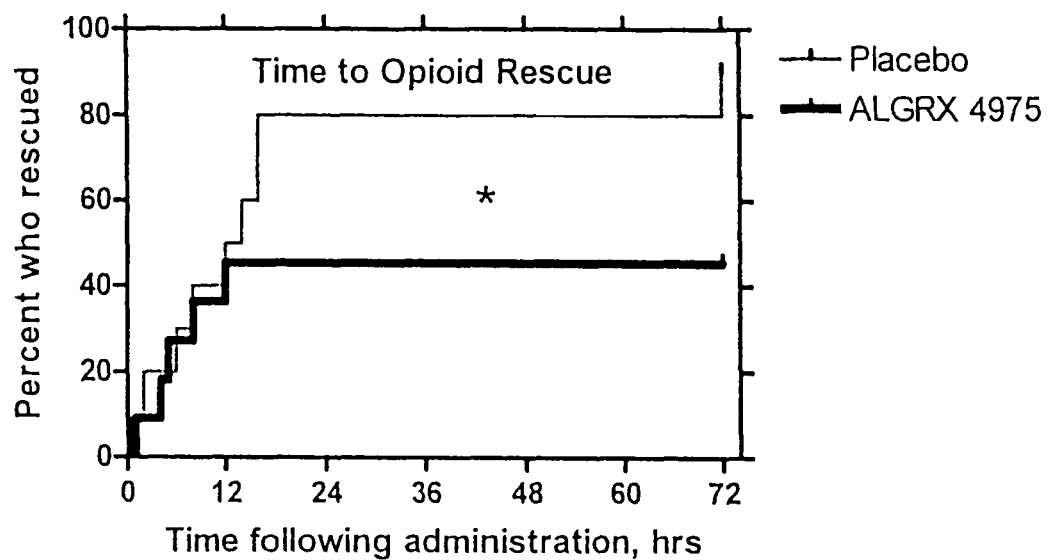
FIG. 5 is a graph displaying a comparison of the percent of subjects entered in to the Bunionectomy Efficacy study exemplified in Example 3 requiring rescue medication.

The results of the bunionectomy study proved that capsaicin administered at a dose of 1000 µg into the wound prior to wound closure reduced both pain score as well as the use of rescue as shown in FIGS. 3 and 4. Reduction in rescue was almost always associated with maintenance of VAS score, i.e., the new drug simply substitutes for the old drug (See; Table 4 below):

TABLE 4

| Time  | Placebo       | purified capsaicin |
|-------|---------------|--------------------|
| 1 hr  | 3.3 +/− 2.3   | 11.1 +/− 7.3       |
| 4 hr  | 3.1 +/− 2.2   | 10.7 +/− 3.6       |
| 8 hr  | 19.7 +/− 4.9  | 5.5 +/− 2.3        |
| 12 hr | 28.1 +/− 9.0  | 8.2 +/− 3.8        |
| 24 hr | 11.7 +/− 4.6  | 1.9 +/− 1.0        |
| 48 hr | 19.3 +/− 8.9  | 5.9 +/− 2.5        |
| 72 hr | 22.9 +/− 9.9  | 10.6 +/− 3.5       | mean +/− SEM n = 10 placebo, n = 11 purified capsaicin
$P < 0.05$ at each time point Administration of 1000 µg of capsaicin prior to wound closure decreased opioid rescue. Only 45% of the study subjects randomized to receive capsaicin required rescue (one subject required rescue at 1 hr, a second subject required rescues at 4 hr, a third subject required rescue at 5 hr, a fourth subject required rescue at 8 hr, and a fifth subject required rescue at 12 hr; 6 subjects did not rescue in 72 hours (n=11)), whereas 80% of the study subjects randomized to receive placebo required rescue (one subject required rescue at 1 hr, a second subject required rescue at 2 hr, a third subject required rescue at 6 hr, a fourth subject required rescue at 8 hr, a fifth subject required rescue at 12 hr, a sixth subject required rescue at 14 hr, a seventh and eighth subject required rescue at 16 hr, and 2 subjects did not require rescue in 72 hours (n=10) $P<0.05$).

Example IV

Epicondylitis Safety and Efficacy Study

The primary objective of the study is to evaluate the safety and efficacy of and to determine the duration of effect of a single dose of capsaicin in subjects with recent onset of acute epicondylitis. The primary efficacy endpoint is the assessment of pain at Day 28 (3 days) as defined by Subject evaluation of pain on movement, measured by the VAS scale at 1 hour, 3 hours, 7 days (2 days) and 28 days (3 days) post-treatment. The secondary efficacy endpoints are: i) subject assessment of symptoms on movement, measured by the 5-point scale at 1 hour, 3 hours, 7 days (2 days) and 28 days (3 days) post-treatment; ii) Investigator assessment of tenderness, measured by the 5-point scale at 1 hour, 3 hours, 7 days (2 days) and 28 days (3 days) post-treatment; iii) Investigator global evaluation of improvement, measured by the 6-point scale at 1 hour, 3 hours, 7 days (2 days) and 28 days (3 days) post-treatment; and iv) subject global evaluation of improvement, measured by the 6-point scale at 1 hour, 3 hours, 7 days (2 days) and 28 days (3 days) post-treatment.

Purified capsaicin is supplied in vials containing 5 mL of purified capsaicin at a concentrations of 500 µg/mL. Study drug is stored at a temperature between 15° C. and 25° C.

Within four hours prior to injection, vehicle is used to dilute the drug to final concentrations of purified capsaicin, as follows:

TABLE 5

| Dose | Concentration | Total Volume of Dose |
|---|---|---|
| 600 µg | 300 µg/ml | 2 ml |

Each vial is used for one subcutaneous injection only and appropriately labeled. The supplier of the purified capsaicin is FormaTech, Inc., 200 Bullfinch Drive, Andover, Mass. 01810. The vials are supplied in bulk to the study center with each vial labeled according to the contents of the vial. The Pharmacist/Study Nurse, who prepares the injection, maintains the investigational product in a lockable cabinet at the required temperature, 15-25° C. The study blind is maintained by the Pharmacist/Study Nurse.

Placebo vehicle for purified capsaicin is supplied in vials containing 5 mL. Local anesthetic (Lignocaine 2%) is used for each subcutaneous injection.

Patient evaluation of pain on movement, measured by a Visual Analog Scale (VAS) is analyzed using an analysis of covariance model covering on the baseline VAS score. Investigator global evaluation of improvement and Patient global evaluation of improvement is analyzed using a Cochran Mantel-Haenszel test.

Each subject is asked to provide a Numerical Pain Scale value for pain immediately upon injection, pain after 1 hour, and pain after 3 hours. Vital signs and physical examination are collected at baseline (Visit 1) and Visit 4. Routine clinical hematology, clinical chemistry and urinalysis measurements will be made prior to dosing (Visit 1) and again at Day 28 (3 days). Safety and tolerability of purified capsaicin is assessed by the collection, review and analysis of adverse events reported during the course of the study.

This is a Phase II, multicenter, randomized, double-blind, placebo-controlled, fixed dose design study to assess the efficacy and safety of a single administration, by subcutaneous injection of 600 µg of capsaicin or placebo in the treatment of acute epicondylitis.

Study treatment is administered to 40 subjects (20 randomized to receive 600 µg of capsaicin and 20 randomized to receive placebo).

Each study subject has four (4) study visits: Baseline visit (day −7±4 days); Visit 2 (Day 0); and Follow-up visits at Day 7 (2 days) and at Day 28 (3 days) after the administration of study treatment.

Visit 1 (day −7±4 days) baseline assessments are initiated, which include medical history, physical exam, vital signs, review of concomitant medication use, elbow pain history, clinical evaluation of the elbow as follows: i) subject's assessment of symptoms on movement (0=none; 1=mild; 2=moderate; 3=severe; 4=very severe); ii) subject's evaluation of pain on movement (100 mm VAS where 0=no pain and 100=worst imaginable); and iii) investigator's assessment of tenderness (0=no tenderness; 1=mild tenderness; 2=moderate tenderness; 3=severe tenderness; 4=very severe tenderness). A review of inclusion/exclusion criteria as well as laboratory assessments are conducted.

At Visit 2 (Day 0), subjects are evaluated for eligibility. A review of concomitant medication use is conducted with changes from Visit 1 recorded in subject's CRF. Clinical evaluation of elbow—pre-dose: i) subject assessment of symptoms on movement (5-point scale); ii) subject's evaluation of pain on movement (VAS); and Investigator assessment of tenderness (5-point scale). Eligible study subjects are randomized to receive either capsaicin 600 µg or placebo. Study drug is administered according to the following procedure: the study subject is positioned in the sitting position with their elbow resting flexed on a firm surface. Aseptic technique is observed. The skin around the site of administration is cleaned. Then up to 1.0 mL of 2% lidocaine is injected by deep subcutaneous injection into muscle and tissue 1 cm distal to the lateral/medial epicondyle and aiming towards the tender spot, 10 minutes prior to injection with study drug. Study drug is then injected and firm pressure is applied to the injection site.

Once the study drug is administered, the study subject is asked to provide an NPS value for pain immediately upon injection, and 1 and 3 hours after injection. Clinical evaluation of the elbow is performed at 1 and 3 hours after injection utilizing the following evaluation parameters: i) subject's evaluation of pain on movement (VAS); subject assessment of symptoms on movement (5-point scale); iii) Investigator assessment of tenderness (5-point scale); iv) Investigator's Global Evaluation of Improvement (−1=worse; 0=no change; 1=slight improvement; 2=moderate improvement; 3=marked improvement; and 4=no symptoms); and v) subject's Global Evaluation of Improvement (−1=worse; 0=no change; 1=slight improvement; 2=moderate improvement; 3=marked improvement; 4=no symptoms). A review of adverse events is conducted.

Some subjects receiving capsaicin may experience a short-lived painful burning sensation post-injection. This is usually adequately controlled by the application of ice packs until the symptoms have resolved, or until a maximum of 20 minutes have passes. (which ever is shorter). However, when additional analgesic management is required, a bolus injection of morphine is administered, which is preceded by a single bolus injection of granisetron (3 mg). Additionally, rescue medication in the form of paracetamol 500 mg tablets, will be provided to all subjects at Visit 2 (Day 0). Subjects will be instructed to take 2 paracetamol tablets (1 gm) every 4-6 hours up to a maximum of 4 g/day if break through pain occurs.

On Visit 3 (day 7±2 days) the study subject is evaluated as follows: First, use of concomitant medications are evaluated. Changes from Visit 2 are recorded on the study subject's CRF. A clinical evaluation of the elbow is performed utilizing the following evaluation parameters: i) subject's evaluation of pain on movement (VAS); ii) subject's assessment of symptoms on movement (5-point scale); iii) investigator's assessment of tenderness (5-point scale); iv) investigator's Global Evaluation of Improvement (6-point scale); and v) subject's Global Evaluation of Improvement (6-point scale). A review of adverse events is conducted.

On Visit 4 (day 28±3 days) the study subject is evaluated (physical exam, vital signs, laboratory assessments). Use of concomitant medication is reviewed with any changes from Visit 3 recorded in the subject's CRF. The following clinical evaluation of the elbow is conducted: i) subject's evaluation of pain on movement (VAS); ii) subject's assessment of symptoms on movement (5-point scale); iii) investigator's assessment of tenderness (5-point scale); iv) investigator's Global Evaluation of Improvement (6-point scale); and v) subject's Global Evaluation of Improvement (6-point scale). A review of adverse events is conducted and the patient is subsequently discharged from the study.

Example V

Shoulder Safety and Efficacy Study

The primary objective of the study is to evaluate the safety and efficacy of and to determine the duration of effect of a single dose of capsaicin in subjects with recent onset of painful shoulder. The primary efficacy endpoint is the assessment of pain and function at Day 28 (3 days) as defined by: i) subject evaluation of pain and disability index on movement, measured by the SPADI scale at 28 days (3 days) post-treatment. The secondary efficacy endpoints are: Subject assessment of SPADI score at 1 hours, 3 hours and 7 days (2 days); ii) subject assessment of symptoms on movement, measured by the 5-point scale at 1 hour, 3 hours, 7 days (2 days) and 28 days (3 days) post-treatment; iii) Investigator assessment of tenderness, measured by the 5-point scale at 1 hour, 3 hours, 7 days (2 days) and 28 days (3 days) post-treatment; iv) Investigator assessment of restricted movement, measured by degree of active/passive abduction, presence of painful arc, active/passive flexion and % of internal/external rotation with resistance at 1 hour, 3 hours, 7 days (2 days) and 28 days (3 days) post-treatment; v) Investigator global evaluation of improvement, measured by the 6-point scale at 1 hour, 3 hours, 7 days (2 days) and 28 days (3 days) post-treatment; subject global evaluation of improvement, measured by the 6-point scale at 1 hour, 3 hours, 7 days (2 days) and 28 days (3 days) post-treatment.

Each subject is asked to provide a Numerical Pain Score value for pain immediately upon injection, pain after 1 hour, and pain after 3 hours. Vital signs and physical examination are collected at baseline (Visit 1) and Visit 4. Routine clinical hematology, clinical chemistry and urinalysis measurements are made prior to dosing (Visit 1) and again at Day 28 (3 days). Safety and tolerability of purified capsaicin is also be assessed by the collection, review and analysis of adverse events reported during the course of the study.

Purified capsaicin is supplied in vials containing 5 mL of purified capsaicin at a concentrations of 500 μg/mL. Study drug is stored at a temperature between 15° C. and 25° C. Within four hours prior to injection, vehicle is used to dilute the drug to final concentrations of purified capsaicin, as follows:

TABLE 6

| Dose | Concentration | Total Volume of Dose |
|---|---|---|
| 600 μg | 300 μg/ml | 2 ml |

Each vial is used for one subcutaneous injection only and appropriately labeled. The supplier of the purified capsaicin is FormaTech, Inc., 200 Bullfinch Drive, Andover, Mass. 01810. The vials are supplied in bulk to the study center with each vial labeled according to the contents of the vial. The Pharmacist/Study Nurse, who prepares the injection, maintains the investigational product in a lockable cabinet at the required temperature, 15-25° C. The study blind is maintained by the Pharmacist/Study Nurse.

Placebo vehicle for purified capsaicin is supplied in vials containing 5 mL. Local anesthetic (Lignocaine 2%) is used for each subcutaneous injection.

This is a Phase II, multicenter, randomized, double-blind, placebo-controlled, fixed dose design study to assess the efficacy and safety of a single administration, by subcutaneous injection of 600 μg of capsaicin or placebo in the treatment of painful shoulder.

Study treatment is administered to 54 subjects (27 randomized to receive 600 μg of capsaicin and 27 randomized to receive placebo).

Each study subject has four (4) study visits: Baseline visit (day −7±4 days); Visit 2 (Day 0); and Follow-up visits at Day 7 (2 days) and at Day 28 (3 days) after the administration of study treatment.

Visit 1 (day −7±4 days) baseline assessments are initiated, which include medical history, physical exam, vital signs, review of concomitant medication use, shoulder pain history, clinical evaluation of the shoulder as follows: i) Shoulder Pain and Disability Index; ii) subject's assessment of symptoms on movement (5-point scale); iii) investigator's assessment of tenderness (5-point scale); and iv) investigator's measurement of restricted movement. A review of inclusion/exclusion criteria as well as laboratory assessments are also conducted.

At Visit 2 (Day 0), subjects are evaluated for eligibility. A review of concomitant medication use is conducted with changes from Visit 1 recorded in subject's CRF. A clinical evaluation of shoulder—pre-dose is performed with using the following: i) Shoulder Pain and Disability Index (SPADI); ii) subject assessment of symptoms on movement (5-point scale); iii) Investigator assessment of tenderness (5-point scale); iv) Investigator's Measurement of Restricted Movement.

Eligible study subjects are randomized to receive either capsaicin 600 μg or placebo. Study drug is administered according to the following procedure: the study subject is positioned in the sitting position. Aseptic technique is observed. The skin around the site of administration is cleaned. Then up to 1.0 mL of 2% lidocaine is administered by subacromial bursa injection, 10 minutes prior to injection of the study drug. Study drug is injected into the subacromial bursa with a 22-gauge 1.5 inch needle inserted into the space between the acromium and the humerus on the lateral aspect of the shoulder. The needle is withdrawn cleanly and firm pressured is applied to the injection site.

Once the study drug is administered, the study subject will be asked to provide an NPS value for pain immediately upon injection, and 1 and 3 hours after injection.

Clinical evaluation of the shoulder is performed at 1 and 3 hours after injection utilizing the following evaluation parameters: i) Shoulder Pain and Disability Index; ii) subject's assessment of symptoms on movement (5-point scale); iii) investigator's assessment of tenderness (5-point scale); iv) investigator's measurement of restricted movement; v) investigator's Global Evaluation of Improvement (−1=worse; 0=no change; 1=slight improvement; 2=moderate improvement; 3=marked improvement; 4=no symptoms); and vi) subject's Global Evaluation of Improvement (6-point scale). A review of adverse events is conducted.

Some subjects receiving capsaicin may experience a short-lived painful burning sensation post-injection. This is usually adequately controlled by the application of ice packs until the symptoms have resolved, or until a maximum of 20 minutes have passes. (which ever is shorter). However, when additional analgesic management be required, a bolus injection of morphine is administered, which is preceded by a single bolus injection of granisetron (3 mg).

On Visit 3 (day 7±2 days) the study subject is evaluated as follows: First, use of concomitant medications are evaluated. Changes from Visit 2 are recorded on the study subject's CRF. A clinical evaluation of the shoulder is performed utilizing the following evaluation parameters: i) Shoulder Pain and Disability Index; ii) subject's assessment of symptoms on movement (5-point scale); iii) investigator's assessment of tenderness (5-point scale); iv) investigator's measurement of restricted movement; v) investigator's Global Evaluation of Improvement (6-point scale); and vi) subject's Global Evaluation of Improvement (6-point scale). A review of adverse events is conducted.

On Visit 4 (day 28±3 days) the study subject is evaluated (physical exam, vital signs, laboratory assessments). Use of concomitant medication is reviewed with any changes from Visit 3 recorded in the subject's CRF. The following clinical evaluation of the shoulder is conducted: i) Shoulder Pain and Disability Index; ii) subject's assessment of symptoms on movement (5-point scale); iii) investigator's assessment of tenderness (5-point scale); iv) investigator's measurement of restricted movement; v) investigator's Global Evaluation of Improvement (6-point scale); and vi) subject's Global Evaluation of Improvement (6-point scale). A review of adverse events is conducted and the patient is subsequently discharged from the study.

Example VI

Median Sternotomy Study

The primary objective of the study is to determine the amount of opioid consumption and postoperative pain scores following median sternotomy for patients receiving purified capsaicin by infiltration and/or injection. Eligible subjects are patients undergoing cardiac, pulmonary, or mediastinal surgery for any indication between the ages of 20-70 years. The operation is performed under general anesthesia and are closely observed in a post-anesthesia care unit as per the practice of the institution. The study drug will be administered to the sternal edges, muscles (e.g., muscle edges), bone (e.g., bone edges), and tissues. All patients will receive standard of care opioid on demand for treatment of pain when transferred to the ward. The dose of capsaicin is administered to the sternal edges, the muscle.

Pain is assessed utilizing VAS 100 mm scale—baseline, every 60 minutes beginning when the patient first is placed in a bedside chair (or ambulated) for 24 hours and then every 4 hours while awake until discharge from the hospital. Patient diaries will be used following discharge for a two-week period.

The primary study endpoint is the time to first request of postoperative opioid. The amount of opioid rescue used is recorded every 24 hours for the first 2 weeks, patients will complete an opioid-related symptom distress (SDS) questionnaire.

Example VII

Chronic Post-Herniorrhapy Study

This study will evaluate the efficacy of purified capsaicin administered by injection for the treatment of chronic post-herniorrhapy pain in subjects who are >6 months after open inguinal herniorrhapy with chronic pain from the surgical area influencing some type of social activities (work, leisure or sports activities, etc.). Study subjects will receive a dose of purified capsaicin in proximity to the surgical site. Pain during rest and well-defined function in relation to factors, which may provoke pain (key end-points) are evaluated. In addition, QST assessment of the surgical area before and after therapy is conducted.

Example VIII

Laparoscopic Cholecystectomy Study

The primary objective of this study is to evaluate the amount of opioid consumption and postoperative pain scores following laparoscopic cholecystectomy in patients administered purified capsaicin by infiltration and/or injection. Study subjects will receive a dose of purified capsaicin in proximity to the surgical site.

This study includes 40 patients (20 randomized to receive capsaicin study drug and 20 randomized to receive placebo study drug) between the ages of 20-60 years old with symptomatic gallstones. The operation is performed under general anesthesia and the subject is closely observed in a post-anesthesia care unit for up to 24 hours and remains in the hospital (typically for 1 to 5 days). All patients receive standard of care opioid on demand for treatment of pain before discharge, and opioid (to be determined) post discharge. Pain is assessed utilizing VAS 100 mm scale—baseline, every 30 minutes till the 2nd postoperative hour then every 4 hours the following 12 hours, an at 24 hours and at days 2, 3, 4, 5, 6 and 7. Patient diaries are used following discharge. Study subject will receive a dose of purified capsaicin 1000-3000 µg divided over the 4 part wounds-infiltrated along the cut muscle edges.

The primary study endpoint is the time to first request of postoperative analgesia The amount of opioid rescue is every 24 hours for the first 3 days, patients complete an opioid-related symptom distress (SDS) questionnaire.

Example IX

Morton's Neuroma Study

The primary objective of the study is to determine the short and intermediate term benefit of purified capsaicin administration by injection in subjects with Morton's Neuroma.

Subjects with pain in the ball of the foot, often radiating into the 3rd and 4th toes, with localized intermetatarsal tenderness diagnostic of Morton's Neuroma, Anteroposterior and lateral radiographs of the involved foot that reveal evidence of no other bony or soft tissue disorders, patients who have previously responded to local anesthetics, steroid injections, or have amputation neuroma are eligible for the study. Study subjects will receive a dose of purified capsaicin at the site, and baseline pain is assessed utilizing a patient diary based on a 100 mm VAS scale. For inclusion in the trial, mean pain score for the 5 days prior to randomization must be greater than 40 mm.

The endpoint of the study is pain measured on a 100 mm VAS, as assessed in the patient diary. Pain scores are averaged on a weekly basis for the 8 weeks following injection. Patients will continue to be followed long-term (minimum 4 months).

In the preceding specification, the invention has been described with reference to specific exemplary embodiments. Those skilled in the art will recognize, or be able to ascertain using no more than routine experimentation, many equivalents to the specific embodiments to the methods described herein. Such equivalents are intended to be encompassed by the following claims.

Example X

Knee Replacement Study

The primary objective of the study is to evaluate the amount of opioid consumption and postoperative pain scores following knee replacement surgery for patients receiving administration of purified capsaicin by infiltration.

This study includes 80 patients (20 patients are randomized to receive placebo, 20 randomized to receive capsaicin 300 µg, 20 randomized to receive capsaicin 1000 µg, and 20 randomized to receive capsaicin 2000 µg). Eligible subjects are patients who undergoing knee replacement surgery between the ages of 20-70 years old.

The knee replacement operation is performed under general anesthesia and is closely observed in a post-anesthesia care unit as per the practice of the institution. All patients receive standard of care opioid on demand for treatment of pain once transferred to the ward. The volume of capsaicin administered into the wound opening during closure ranges from about 5 ml to about 10 ml.

Pain is assessed utilizing VAS 100 mm scale—baseline, every 60 minutes beginning when the patient first is placed on mechanical flexion/extension for 24 hours and then every 4 hours while awake until discharge from the hospital. Patient diaries are used following discharge for a two-week period.

Example XI

Mastectomy Study

Mastectomy results in significant pain and requires substantial doses of opioids postoperatively. Analgesic techniques that provide good pain control while minimizing opioid side effects are thus highly desirable. The primary objective of the study determines the amount of opioid consumption and postoperative pain scores following mastectomy for patients receiving capsaicin.

The study includes 80 patients (20 patients are randomized to receive placebo, 20 randomized to receive capsaicin 300 µg, 20 randomized to receive capsaicin 1000 µg, and 20 randomized to receive capsaicin 2000 µg). Eligible patients include patients undergoing mastectomy between the ages of 20-70 years old. The operation is performed under general anesthesia and is closely observed in a post-anesthesia care unit as per the practice of the institution. All patients receive standard of care opioid on demand for treatment of pain once transferred to the ward.

The dose of study drug is administered by infiltration in a volume from about 5 ml to about 10 ml within the wound cavity during closure.

Pain is assessed utilizing VAS 100 mm scale—baseline, every 60 minutes beginning when the patient first is placed on mechanical flexion/extension for 24 hours and then every 4 hours while awake until discharge from the hospital. Patient diaries are used following discharge for a two-week period.

The primary endpoint is time to first request of postoperative opioid. Opioid rescue occurs every 24 hours for the first 2 weeks, patients complete an opioid-related symptom distress (SDS) questionnaire.

CONCLUSION

The invention has been described in an illustrative manner, and it is to be understood that the particular embodiments of the capsaicinoid formulations and methods of treatment described herein are intended to be descriptive rather than limiting. Many modifications and variations of the methodologies and formulations disclosed herein are possible in light of the above teachings, and such obvious modifications are deemed to be encompassed within the scope of the appended claims.

What is claimed is:

1. A method for attenuating pain in a joint in a human or animal, comprising:
   injecting into an intraarticular space or intrasynovially in the joint of a human or animal in need thereof an effective amount of a capsaicinoid at a joint afflicted with osteoarthritis in a pharmaceutically acceptable carrier for injection in an amount effective to attenuate pain emanating from the joint for at least one month, the effective amount being from about 1 µg to about 5000 µg of capsaicin or a therapeutically equivalent dose of a capsaicinoid other than capsaicin.

2. The method of claim 1, wherein from about 10 to about 3000 µg of capsaicin is administered per injection.

3. The method of claim 1, wherein from about 300 to about 1500 µg of capsaicin is administered per injection.

4. The method of claim 1, wherein from about 400 to about 1200 µg of capsaicin is administered per injection.

5. The method of claim 1, wherein the pharmaceutically acceptable carrier comprises an agent selected from the group consisting of antimicrobial agents, isotonic agents, buffers, antioxidants, local anesthetics, suspending and dispersing agents, emulsifying agents, sequestering agents, chelating agents and any combinations thereof.

6. The method of claim 1, wherein the capsaicin is injected into the articular space or synovial fluid of a joint selected from the group consisting of knee, elbow, hip, sternoclavicular, temporomandibular, shoulder, hand, foot, spinal, carpal, tarsal, wrist, ankle, and intervertebral disk.

7. The method of claim 1, wherein the capsaicinoid is injected in the form of injectable microparticles.

8. The method of claim 1, further comprising administering a local anesthetic prior to or concurrently with the capsaicinoid in an amount and location effective to attenuate an initial hyperalgesic effect of the capsaicinoid.

9. The method of claim 8, wherein the local anesthetic is administered by direct injection into the site where the capsaicinoid is injected.

10. The method of claim 1, further comprising administering phenol prior to or concurrently with the capsaicinoid in an amount and location effective to attenuate an initial hyperalgesic effect of the capsaicinoid.

11. The method of claim 1, wherein said capsaicinoid is selected from the group consisting of resiniferatoxin, N-vanillylnonanamides, N-vanillylsulfonamides, N-vanillylureas, N-vanillylcarbamates, N[(substituted phenyl)methyl] alkylamides, methylene substituted N[(substituted phenyl)methyl]alkanamides, N[(substituted phenyl)methyl]-cis-monosaturated alkenamides, N[(substituted phenyl)methyl] diunsaturated amides, 3-hydroxyacetanilide, hydroxyphenylacetamides, pseudocapsaicin, dihydrocapsaicin, nordihydrocapsaicin anandamide, piperine, zingerone, warburganal, polygodial, aframodial, cinnamodial, cinnamosmolide, cinnamolide, isovelleral, scalaradial, ancistrodial, β-acaridial, merulidial, scutigeral, and any combinations thereof.

12. The method of claim 1, wherein said capsaicinoid is capsaicin.

13. The method of claim 12, wherein said capsaicin consists essentially of trans-capsaicin.

14. The method of claim 1, wherein said capsaicinoid comprises a mixture of capsaicinoids in a total amount equivalent to a capsaicin dose from about 1 µg to about 5000 µg of capsaicin.

15. The method of claim 1, further comprising administering to the human or animal an analgesically effective amount of an analgesic.

16. The method of claim 1, wherein the pain is associated with osteoarthritis of the hip, comprising injecting capsaicin intraarticulary into the hip.

17. The method of claim 1, wherein the pain is associated with osteoarthritis of the shoulder, comprising injecting capsaicin intraarticulary into the shoulder.

18. The method of claim 1, wherein the pain is associated with osteoarthritis of the spine, comprising injecting capsaicin intraarticulary into the spine.

19. The method of claim 1, wherein the pain is associated with osteoarthritis of the elbow, comprising injecting capsaicin intraarticulary into the elbow.

20. The method of claim 1, wherein the pain is associated with osteoarthritis of the foot, comprising injecting capsaicin intraarticulary into the foot.

21. The method of claim 1, wherein the pain is associated with osteoarthritis of the hand, comprising injecting capsaicin intraarticulary into the hand.

22. The method of claim 1, wherein the dose of capsaicin is from about 1 to about 3000 μg.

23. The method of claim 1, wherein the dose of capsaicin is from about 20 to about 300 μg.

24. The method of claim 1, wherein the dose of capsaicin is from about 35 to about 200 μg.

25. The method of claim 1, wherein the dose of capsaicin is 100 μg.

26. The method of claim 1, wherein the injection of capsaicinoid intraarticularly into the joint attenuates pain emanating from the joint for at least 3 months.

27. The method of claim 1, wherein the injection of capsaicinoid intraarticularly into the joint attenuates pain emanating from the joint for up to six months.

28. The method of claim 15, wherein the analgesic is selected from the group consisting of sodium aurothiomalate, nonsteroidal anti-inflammatory agents (NSAID), opioid analgesics, paraminophenol derivatives and salicylates.

\* \* \* \* \*

UNITED STATES PATENT AND TRADEMARK OFFICE
CERTIFICATE OF CORRECTION

| | | |
|---|---|---|
| PATENT NO. | : 8,420,600 B2 | Page 1 of 1 |
| APPLICATION NO. | : 11/499995 | |
| DATED | : April 16, 2013 | |
| INVENTOR(S) | : Burch et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 968 days.

Signed and Sealed this
Sixteenth Day of December, 2014

Michelle K. Lee
*Deputy Director of the United States Patent and Trademark Office*